United States Patent [19]

Allen et al.

[11] Patent Number: 5,145,965
[45] Date of Patent: Sep. 8, 1992

[54] 2,6-METHANOPYRROLO-3-BENZAZO-CINES

[75] Inventors: Richard C. Allen, Flemington; David G. Wettlaufer, Phillipsburg, both of N.J.

[73] Assignee: Hoechst-Roussel Pharmaceuticals Incorporated, Somerville, N.J.

[21] Appl. No.: 666,394

[22] Filed: Mar. 11, 1991

Related U.S. Application Data

[60] Division of Ser. No. 483,474, Feb. 22, 1990, Pat. No. 5,037,985, which is a division of Ser. No. 272,045, Nov. 16, 1988, Pat. No. 4,929,622, which is a continuation-in-part of Ser. No. 101,716, Sep. 24, 1987, abandoned.

[51] Int. Cl.$^5$ .................. C07D 471/08; C07D 221/22
[52] U.S. Cl. ................................ 546/63; 546/97
[58] Field of Search ........................ 546/63, 97

[56] References Cited

U.S. PATENT DOCUMENTS

| | | | |
|---|---|---|---|
| 3,331,849 | 7/1967 | Shavel et al. | 546/63 |
| 3,382,249 | 5/1968 | Albertson | 546/97 |
| 3,686,213 | 8/1972 | Poletto et al. | 546/97 |
| 3,882,236 | 5/1975 | Molloy | 546/97 |
| 4,032,529 | 6/1977 | Wentland et al. | 546/97 |
| 4,127,577 | 11/1978 | Wentland et al. | 546/97 |
| 4,205,171 | 5/1980 | Albertson | 546/97 |
| 4,239,890 | 12/1980 | Michne | 546/97 |
| 4,255,579 | 3/1980 | Michne | 546/97 |
| 4,296,238 | 10/1981 | Michne | 546/97 |
| 4,322,533 | 5/1982 | Lesher et al. | 546/273 |
| 4,335,243 | 6/1982 | Michne | 546/97 |

FOREIGN PATENT DOCUMENTS

| | | | |
|---|---|---|---|
| 308913 | 3/1989 | European Pat. Off. | 546/63 |
| 2407671 | 9/1974 | Fed. Rep. of Germany | 546/63 |

OTHER PUBLICATIONS

Baker et al. J. Org. Chem. 17 pp. 149 to 156 (1962).
Asselin et al. J. Med. Chem. 1986, 29 648-654.

*Primary Examiner*—Robert T. Bond
*Assistant Examiner*—E. C. Ward
*Attorney, Agent, or Firm*—Elliott Korsen

[57] ABSTRACT

Novel 2,6-methanopyrrolo-3-benzazocines, intermediates, processes for the preparation thereof, and methods for alleviating pain utilizing compounds or compositions thereof are disclosed.

1 Claim, No Drawings

2,6-METHANOPYRROLO-3-BENZAZOCINES

This is a division, of application Ser. No. 483,474 filed Feb. 22, 1990, now U.S. Pat. No. 5,037,985, which is a divisional of Ser. No. 272,045 filed Nov. 16, 1988, now U.S. Pat. No. 4,929,622, which is a continuation-in-part of Ser. No. 101,716, filed Sep. 24, 1987, now abandoned.

This invention relates to 2,6-methanopyrrolo-3-benzazocines. More particularly, this invention relates to a compound of the formula

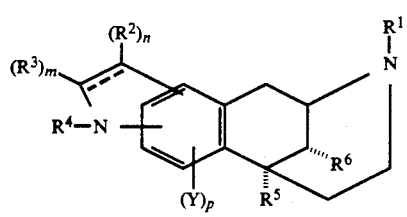

Formula I wherein $R^1$ is selected from the group consisting of hydrogen, loweralkyl, loweralkenyl, cycloalkylloweralkyl, arylloweralkyl, arylaminoloweralkyl, cyano, and —C(O)$R^9$ wherein $R^9$ is hydrogen, loweralkyl, or loweralkoxy; $R^2$ and $R^3$ are independently selected from the group consisting of loweralkyl, arylloweralkyl, halogen, oxo and —C(O)$R^7$ wherein $R^7$ is selected from the group consisting of hydrogen, loweralkyl, aryl, arylloweralkyl, hydroxy, loweralkoxy, arylloweralkoxy, aryloxy, and amino; $R^4$ is selected from the group consisting of hydrogen, loweralkyl, arylloweralkyl and —C(O)$R^8$ wherein $R^8$ is selected from the group consisting of hydrogen, arylloweralkyl, aryl, loweralkyl, loweralkoxy, arylloweralkoxy, and aryloxy; $R^5$ and $R^6$ are independently hydrogen or loweralkyl, or taken together are a bivalent radical of the formula —(CH$_2$)$_4$—; m, n, and p are integers independently having values of zero or 1 with the proviso that the sum of m and n only exceeds 1 when at least one of $R^2$ and $R^3$ is linear loweralkyl, halogen, or oxo; Y is halogen or loweralkyl; and the dotted line in said compound is an optional bond; the geometrical isomers, optical antipodes or pharmaceutically acceptable acid addition salts thereof, which, alone or in combination with inert adjuncts, are useful in alleviating pain.

Of particular interest are 2,6-methanopyrrolo-3-benzazocines of the formulas:

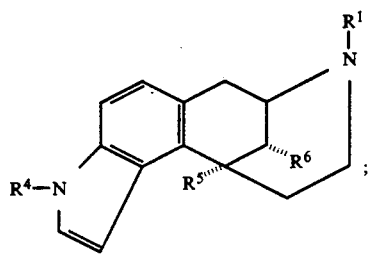

Formula IIa

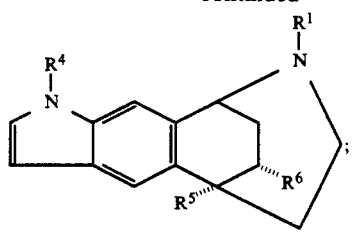

Formula IIb

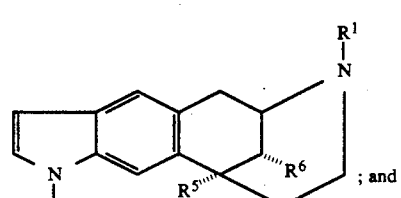

Formula IIc

; and

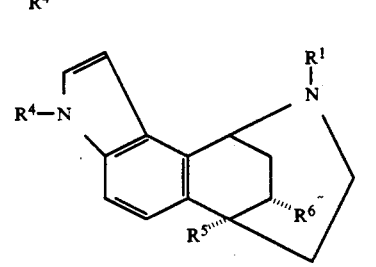

Formula IId wherein $R^1$, $R^4$, $R^5$ and $R^6$ are as previously described.

Subgeneric to the 2,6-methanopyrrolo-3-benzazocines of this invention are Formula I compounds wherein:
(a) $R^1$ is hydrogen;
(b) $R^1$ is loweralkyl;
(c) $R^1$ is cycloalkylloweralkyl;
(d) $R^1$ is loweralkenyl;
(e) $R^1$ is arylloweralkyl;
(f) $R^1$ is —C(O)$R^9$ wherein $R^9$ is as previously defined;
(g) $R^2$ and $R^3$ are independently selected from the group consisting of loweralkyl, arylloweralkyl, halogen, oxo, and —C(O)$R^7$ as previously defined;
(h) $R^2$ and $R^3$ are oxo;
(i) $R^4$ is hydrogen;
(j) $R^4$ is loweralkyl;
(k) $R^4$ is arylloweralkyl;
(l) $R^4$ is —C(O)$R^8$ as previously defined;
(m) $R^5$ and $R^6$ are independently hydrogen or loweralkyl;
(n) $R^5$ and $R^6$ taken together are a bivalent radical of the formula —(CH$_2$)$_4$—;
(o) p is zero;
(p) $R^1$ is arylaminoloweralkyl; and
(q) $R^1$ is cyano.

In a further embodiment this invention relates to intermediates of the formula

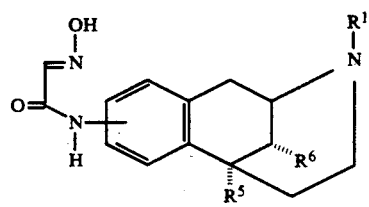

Formula III wherein $R^1$ is selected from the group consisting of hydrogen, loweralkyl, loweralkenyl, cycloalkylloweralkyl, arylloweralkyl and —C(O)$R^9$ wherein $R^9$ is hydrogen, loweralkyl or loweralkoxy; and $R^5$ and $R^6$ are independently hydrogen or loweralkyl, or taken together are a bivalent radical of the formula —(CH$_2$)$_4$—, which have utility in the production of the hereinbeforementioned 2,6-methanopyrrolo-3-benzazocines.

As used throughout the specification and appended claims, the following definitions shall apply:

"Loweralkyl" —a linear or branched, acyclic hydrocarbon radical containing no unsaturation and having the formula —C$_x$H$_{2x+1}$ wherein x is an integer having a value of 1 to 7 inclusive, such as methyl, ethyl, 1-propyl, 2-propyl, 1-butyl, 1-pentyl, 2-pentyl, 3-hexyl, 4-heptyl, and the like. Preferred loweralkyls are those radicals wherein x has a value of 1 to 3 inclusive, most preferably 1 to 2.

"Loweralkenyl" —a linear or branched, acyclic hydrocarbon radical having one olefinic bond and represented by the formula: —C$_x$H$_{2x-1}$, wherein x is an integer having a value of 3 to 7 inclusive, such as 2-propenyl, 3-butenyl, 3-pentenyl, 3-hexenyl, 6-heptenyl, and the like. Preferred loweralkenyls are those radicals wherein x has a value of 3 to 5 inclusive, and, most preferably, is 3.

"Cycloalkyl" —a cyclic hydrocarbon radical of the formula —C$_x$H$_{2x-1}$ wherein x is an integer having a value of 3 to 7 inclusive, such as cyclopropyl, cyclobutyl, cyclopentyl, and cycloheptyl. Preferred cycloalkyls are those radicals wherein x has a value of 3 to 6 inclusive, and, most preferably is 3.

"Cycloalkylloweralkyl" —a loweralkyl group having a cycloalkyl substituent thereon.

"Loweralkoxy" —an acyclic organic radical of the formula —OC$_x$H$_{2x+1}$ wherein x is an integer having a value of 1 to 7 inclusive, such as methoxy, ethoxy, 1- and 2-propoxy, 1,2-dimethylethoxy, 1-butoxy, 1- and 2-pentoxy, 3-hexoxy, 4-heptoxy and the like. Preferred loweralkoxys are those radicals wherein x has a value of 1 to 5 inclusive, most preferably, 1 to 3 inclusive.

"Aryl" —a phenyl group optionally substituted by up to 3 substituents each of which is independently loweralkyl, loweralkoxy, halogen, trifluoromethyl, nitro or cyano.

"Loweralkoxycarbonyl" —an acyclic organic radical of the formula —C(O)OC$_x$H$_{2x+1}$ wherein x is an integer having a value from 1 to 5 inclusive, such as methoxycarbonyl, ethoxycarbonyl, 1- and 2-propoxycarbonyl, 1-butoxycarbonyl, 1- and 2-pentoxycarbonyl and the like. Preferred loweralkoxycarbonyls are those radicals wherein x has a value of 1 to 4 inclusive, and most preferably, is 1 or 2.

"Halogen" —a member of the group consisting of fluorine, chlorine, bromine or iodine radicals.

"Arylloweralkyl" —a loweralkyl group having an aryl substituent thereon.

"Aryloxy" —a monovalent radical which consists of an aryl group linked through an ether oxygen and having its free valence bond from the ether oxygen.

Then 2,6-methanopyrrolo-3-benzazocines of this invention are synthesized by the process illustrated in the Reaction Schemes which follow.

To prepare the parent system, 2,6-methanopyrrolo-3-benzazocine diones, a nitro-substituted 1,2,3,4,5,6-hexahydro-2,6-methano-3-benzazocine 1 is reduced to the corresponding amino-substituted benzazocine 2, which is converted to an isonitrosoacetanilide 3, which in turn is cyclized to an isatin 4. See Reaction Scheme A.

The preparation of nitro-substituted 1,2,3,4,5,6-hexahydro-2,6-methano-3-benzazocines is well known in the art. Conventional preparations include the nitration of 1,2,3,4,5,6-hexahydro-2,6-methano-3-benzazocines by treatment with nitric acid in an appropriate solvent (e.g. glacial acetic acid or sulfuric acid). Alkylation of the nitro substituted secondary benzazocine with a halide of the formula $R^1X$ wherein $R^1$ is loweralkyl, loweralkenyl, cycloalkylloweralkyl, arylloweralkyl or —C(O)$R^9$ as previously described, and X is halogen, preferably chlorine or bromine, provides a nitro-substituted benzazocine having a group $R^1$ at the nitrogen atom in the 3-position of the benzazocine ring. Where $R^1$ is methyl, removal of the methyl group to give the secondary amine is achieved by reaction with an appropriate haloformate such as, for example, 1-chloroethyl chloroformate, followed by methanolysis. The alkylation of the nitro-substituted benzazocine is ordinarily conducted in an inert organic solvent in the presence of an appropriate acid acceptor (e.g. an alkali metal carbonate and/or bicarbonate such as, for example, sodium carbonate, sodium bicarbonate, potassium carbonate, potassium bicarbonate, and the like). Suitable solvents include polar aprotic solvents such as dimethylformamide, dimethylacetamide, dimethylsulfoxide, and the like, alkanols such as propanol and n-butanol; and acetone. Dimethylformamide is preferred. See, for example, U.S. Pat. Nos. 4,255,579, 4,127,577 and 4,032,529 all assigned to Sterling Drug Inc., setting forth the nitration and subsequent alkylation of 1,2,3,4,5,6-hexahydro-2,6-methano-3-benzazocines in greater detail.

Reduction of the nitro-substituted benzazocine 1 is also accomplished by conventional methods which include both catalytic hydrogenation in the presence of a noble metal catalyst (e.g. platinum, rhodium, palladium, and the like) and chemical reduction. Catalytic hydrogenation is ordinarily conducted in the presence of an alkanol solvent (e.g. methanol, ethanol, 1- and 2-propanol, and the like, and mixtures thereof) at a temperature of from about 20° C. to about 75° C. and a hydrogen gas pressure of from about 16 psig to about 65 psig. Preferably, catalytic hydrogenation is conducted at a temperature of from about 20° C. to about 30° C. and a hydrogen gas pressure of from about 50 psig to about 60 psig, in the presence of methanol employing 5% palladium on barium sulfate as the catalyst. Chemical reduction of the nitro-substituted benzazocine may be achieved utilizing a metal (e.g. iron) and a mineral acid (e.g. hydrochloric acid) as described more fully in the above cited U.S. Patents assigned to Sterling Drug Inc.

The conversion of the amino-substituted benzazocine 2 to an isatin 4 is similarly accomplished utilizing techniques which are well known in the art. See, for example, the procedures described in A. A. Asselin et al., J. Med. Chem. 29, 648 (1986). Typically, the amino-substituted benzazocine 2 is treated with hydroxylamine hydrochloride and chloral hydrate in the presence of an anhydrous alkali metal sulfate (e.g. potassium sulfate, sodium sulfate, and the like, sodium sulfate being preferred). The reaction is ordinarily conducted in the presence of water or dilute hydrochloric acid at a temperature of from about 80° C. to the reflux temperature of the solvent medium, preferably at reflux. Cyclization of the resulting isonitrosoacetanilide 3 is achieved by treatment with an appropriate acid (e.g. mineral acids such as hydrochloric, sulfuric, and phosphoric acid, aqueous sulfuric acid being preferred) at a temperature of from about 70° C. to about 85° C., preferably from about 70° C. to about 75° C., to yield the isatin 4.

The reduction of the parent 2,6-methanopyrrolo-3-benzazocine dione system to hexahydro- and octahydro-2,6-methanopyrrolo-3-benzazocines is illustrated in Reaction Scheme B. As illustrated, reduction of an isatin 6 wherein $R^1$ is loweralkyl provides the corresponding hexahydro- and octahydro-2,6-methanopyrrolo-3-benzazocines 7 and 8. Reduction to the hexahydro-2,6-methanopyrrolo-3-benzazocine 7 is ordinarily conducted in the presence of an inert organic solvent (e.g. ethereal solvents such as dioxane, diethyl ether, tetrahydrofuran, and the like; tetrahydrofuran being preferred) utilizing a reducing agent such as lithium aluminum hydride or borane. The reduction is ordinarily carried out at a temperature of from about 0° C. to the reflux temperature of the solvent medium, preferably at reflux. Desirably the reduction is conducted under an inert atmosphere. It should be noted that the reduction of isatins 5 wherein $R^1$ is a radical of the formula —C(O)$R^9$ as previously described can result in the simultaneous reduction of the acyl group, providing an alternative mechanism for the synthesis of loweralkyl-substituted benzazocines 7.

Further reduction of hexahydro-2,6-methano-pyrrolo-3-benzazocines 7 by treatment with a reducing agent such as, for example, an alkali metal organoborohydride such as sodium cyanoborohydride yields the corresponding octahydro-2,6-methanopyrrolo-3-benzazocine 8. This subsequent reduction is ordinarily conducted at a reduced temperature of from about 15° C. to about 20° C. in the presence of an alkanoic acid (e.g. formic, acetic, 1- and 2-propionic acid, and the like, acetic acid being preferred).

2,6-Methanopyrrolo-3-benzazocines wherein $R^1$ is hydrogen may be furnished by cleaving a loweralkyl-substituted benzazocine 9 protected at the nitrogen atom of the pyrrolo ring to an unsubstituted benzazocine 10, and then removing the protecting group of 10 to afford the benzazocine 11.

Protection of the pyrrolo nitrogen atom is achieved by conventional manipulation techniques. For example, a loweralkyl-substituted benzazocine 7 may be reacted with a strong base (e.g. an alkali metal hydride such as sodium hydride, or potassium hydride, or lithium bis(-trimethylsilyl)amide) in a suitable solvent medium (e.g. a polar aprotic solvent such as dimethylformamide, dimethylsulfoxide, dimethylacetamide, hexamethylphosphoramide, and the like or an ethereal solvent such as tetrahydrofuran) at a temperature of from about −80° C., to about 80° C., and then treated with an arylloweralkylsulfonyl halide or arylsulfonylhalide (e.g. benzenesulfonyl chloride, toluenesulfonyl chloride, and the like) or triisopropylsilyltrifluoromethane sulfonate to give the protected benzazocine 9.

Cleavage of the 3-loweralkyl group is likewise effected by conventional synthetic techniques. For example, the protected benzazocine 9 may be treated with an alkyl-, phenyl- or benzylchloroformate (e.g. ethyl chloroformate, 1-chloroethyl chloroformate, phenyl chloroformate, benzyl chloroformate, and the like) and the resulting carbamate hydrolyzed to the unsubstituted benzazocine 10. Optionally, the chloroformate treatment is conducted in the presence of an alkali metal carbonate and/or bicarbonate such as, for example, sodium carbonate, potassium carbonate, sodium bicarbonate, potassium bicarbonate, and the like, or in the presence of a tertiary amine such as, for example, triethylamine, diisopropylethylamine, and the like. Hydrolysis of the carbamate intermediate may be achieved by treatment with a suitable base (e.g. an alkali metal hydroxide such as, for example, potassium, sodium, and lithium hydroxide) in an aqueous alkanol (e.g. methanol, ethanol, 1- and 2-propanol and the like) at a temperature of from about 25° to the reflux temperature of the solvent medium, or in the case of the 1-chloroethyl carbamate by methanolysis.

Well known techniques are similarly available for removal of the protecting group at the nitrogen atom of the pyrrolo ring. For example, refluxing the protected benzazocine 10 in the presence of an alkali metal aluminum hydride (e.g. lithium aluminum hydride, sodium bis (2-methoxyethoxy)aluminum hydride, and the like) in an appropriate solvent medium (e.g. ethereal solvents such as, for example, tetrahydrofuran, 1,2-dimethoxyethane, bis(2-methoxyethyl)ether, diethyl ether, and dioxane) or, in the case of the triisopropylsilyl group, treatment with tetra-n-butyl-ammonium fluoride in tetrahydrofuran. The resultant hexahydro-2,6-methanopyrrolo-3-benzazocine 11 may be reduced as previously described in the context of loweralkyl-substituted hexahydro-2,6-methanopyrrolo-3-benzazocines to the corresponding octahydrobenzazocines 12.

Alternatively, 2,6-methanopyrrolo-3-benzazocines 11 are prepared directly from benzazocines 7 wherein the pyrrolo nitrogen atom is unprotected by condensing a benzazocine 7 with a cyanogen halide, for example, cyanogen bromide, in the presence of a tertiary amine such as, for example, triethylamine, diisopropylethylamine, and the like, in a halocarbon solvent such as, for example, dichloromethane, trichloromethane, 1,2-dichloroethane, and the like, followed by either reductive removal or basic hydrolysis of the cyano function of the resultant of N-cyanobenzazocine 7a. The reductive cleavage of the cyano moiety of 7a is accomplished by means of an alkali metal aluminum hydride, e.g., lithium aluminum hydride, in an ethereal solvent, e.g., tetrahydrofuran. The basic hydrolysis may be performed by contacting an N-cyanobenzazocine 7a with an alkali metal hydroxide, e.g., sodium or potassium hydroxide, in an aqueous system containing, if necessary, a cosolvent, e.g., an aprotic dipolar solvent such as dimethylformamide, hexamethylphosphoramide, and the like.

2,6-Methanopyrrolo-3-benzazocines 14 wherein $R^1$ is loweralkyl, loweralkenyl, cycloalkylloweralkyl or arylloweralkyl may be produced by the alkylation of unsubstituted benzazocines 10 followed by deprotection of the resulting substituted benzazocine 13. Alkylation may be achieved, for example, by treating the unsubstituted benzazocine 10 with a halide of the formula $R^1Z$, wherein Z is chlorine, bromine or iodine and $R^1$ is as previously described, in the presence of a base suspended or dissolved in a suitable solvent. Suitable bases include alkali metal carbonates and bicarbonates such as, for example, potassium bicarbonate, and the like, and tertiary amines such as, for example, triethylamine, diisopropylethylamine and the like. Among the suitable solvents there may be mentioned polar aprotic solvents, chlorinated hydrocarbons, ethereal solvents, and the like, such as, for example, dimethylformamide, dimethylacetamide, bis(2-methoxyethyl ether), dimethoxyethane, dimethylsulfoxide, hexamethylphosphoramide, dichloromethane, diethyl ether, tetrahydrofuran, dioxane, and the like. The alkylation is ordinarily conducted at temperatures of from about 20° C. to reflux. Deprotection of 3-substituted benzazocines 13 and reduction to the corresponding hexahydro-and octahydro-derivatives 14 and 15 is as previously described.

Alternatively, a benzazocine 14 wherein $R^1$ is as above is prepared by the alkylation of a pyrrolo N-unsubstituted benzazocine 11 by the process described above for the conversion of a pyrrolo N-protected benzazocine 10 to benzazocine 14. For example, treatment of benzazocine 11 with an alkylating agent of the formula $R^1Z$ wherein $R^1$ and Z are as described above in the presence of a tertiary amine (e.g., triethylamine or diisopropylethylamine) in a polar aprotic solvent (e.g., dimethylformamide, dimethylacetamide, hexamethylphosphoramide or dimethylsulfoxide) provides directly benzazocine 14 wherein $R^1$ is as above. A promoter such as an alkali metal iodide (e.g., sodium or potassium iodide) may be employed to facilitate the alkylation. The reaction temperature is not narrowly critical. The alkylation is conveniently performed at a temperature between about 0° C. to about 100° C.

The sequence of alkylation, or protection, alkylation and deprotection steps described in the context of the hexahydrobenzazocines of this invention is equally applicable to octahydrobenzazocine.

Included among the compounds of this invention are the following:

3-benzyl-1,2,3,4,5,6-hexahydro-6,12-dimethyl-2,6-methanopyrrolo[3,2-h][3]-benzazocine-7,8(9H)-dione;

3-benzyl-1,2,3,4,5,6-hexahydro-6,12-dimethyl-2,6-methano-9H-pyrrolo[3,2-h][3]-benzazocine;

3-benzyl-1,2,3,4,5,6,7,8-octahydro-6,12-dimethyl-2,6-methano-9H-pyrrolo[3,2-h][3]-benzazocine;

1,2,3,4,5,6,7,8-octahydro-6,12-dimethyl-3-(2-propenyl)-2,6-methano-9H-pyrrolo[3,2-h][3]benzazocine;

1,2,3,4,5,6-hexahydro-6,12-dimethyl-3-(2-propenyl)-2,6-methanopyrrolo[3,2-h][3]benzazocine-7,8(9H)-dione;

3-cyclopropylmethyl-1,2,3,4,5,6-hexahydro-6,12-dimethyl-2,6-methano-9H-pyrrolo[3,2-h][3]benzazocine;

3-cyclopropylmethyl-1,2,3,4,5,6-hexahydro-6,12-dimethyl-2,6-methanopyrrolo[3,2-h][3]benzazocine-7,8(9H)-dione;

3-cyclopropylmethyl-1,2,3,4,5,6,10,11-octahydro-6,12-dimethyl-2,6-methano-9H-pyrrolo[2,3-j][3]benzazocine;

1,2,3,4,5,6-hexahydro-3,6,12-trimethyl-2,6-methano-8H-pyrrolo[2,3-i][3]benzazocine;

1,2,3,4,5,6-hexahydro-3,6,12-trimethyl-2,6-methanopyrrolo[2,3-i][3]benzazocine-9,10(8H)-dione;

1,2,3,4,5,6-hexahydro-3,6,7,12-tetramethyl-2,6-methanopyrrolo[2,3-i][3]benzazocine-9,10(8H)-dione;

1,2,3,4,5,6-hexahydro-3,6,7,12-tetramethyl-2,6-methano-8H-pyrrolo[2,3-i][3]benzazocine;

11-acetyl-1,2,3,4,5,6-hexahydro-3,6,12-trimethyl-2,6-methano-9H-pyrrolo[2,3-j][3]benzazocine;

11-aminocarbonyl-1,2,3,4,5,6-hexahydro-3,6,12-trimethyl2,6-methano-9H-pyrrolo[2,3-j][3]benzazocine;

1,2,3,4,5,6,10,11-octahydro-3,6,12-trimethyl-2,6-methano-9H-pyrrolo[2,3-j][3]benzazocine;

3-benzyl-1,2,3,4,5,6-hexahydro-6,12-dimethyl-2,6-methano-8H-pyrrolo[2,3-i][3]benzazocine;

7-chloro-1,2,3,4,5,6-hexahydro-3,6,12-trimethyl-2,6-methanopyrrolo[2,3-j][3]benzazocine-10,11(9H)-dione;

1,2,3,4,5,6-hexahydro-3,6,12-trimethyl-2,6-methano-9H-pyrrolo[3,2-h][3]benzazocine;

1,2,3,4,4a,5,6,8-octahydro-14-methyl-5,11b-(iminoethano)-11bH-naphth[1,2-f]indole;

1,2,3,4,5,6,7,10-octahydro-14-methyl-5,11b-(iminoethano)-11bH-naphth[2,1-e]indole;

3,6,7,7a,8,9,10,11-octahydro-14-methyl-7,11a-(iminoethano)-11aH-naphth[1,2-e]indole;

1,4,5,5a,6,7,8,9-octahydro-14-methyl-5,9a-(iminoethano)-9aH-naphth[2,1-e]indole;

decahydro-14-methyl-5,11b-(iminoethano)-11bH-naphth[2,1-f]indole;

3,6,7,7a,8,9,10,11-octahydro-14-(2-phenylethyl)-7,11a-(iminoethano)-11aH-naphth[1,2-e]indole;

1,2,3,4,5,6-hexahydro-6,12-dimethyl-3-(2-phenylethyl)-2,6-methano-9H-pyrrolo[3,2-h][3]benzazocine;

1,2,3,4,5,6-hexahydro-6,12-dimethyl-3-(3-methyl-2-butenyl)-2,6-methano-10H-pyrrolo[3,2-i][3]benzazocine;

3-cyclopropylmethyl-1,2,3,4,5,6,9,10-octahydro-6,12-dimethyl-2,6-methano-8H-pyrrolo[2,3-i][3]benzazocine;

1,2,3,4,5,6-hexahydro-6,12-dimethyl-3-(3-methyl-2-butenyl)-2,6-methano-8H-pyrrolo[2,3-i][3]benzazocine;

1,2,3,4,5,6,10,11-octahydro-6,12-dimethyl-3-(2-phenylethyl)-2,6-methano-9H-pyrrolo[2,3-j][3]benzazocine;

1,2,3,4,5,6-hexahydro-6,12-dimethyl-3-(2-phenylethyl)-2,6-methano-10H-pyrrolo[3,2-i][3]benzazocine;

6,12-diethyl-1,2,3,4,5,6-hexahydro-3-methyl-2,6-methano-8H-pyrrolo[2,3-i][3]benzazocine;

6,12-diethyl-1,2,3,4,5,6-hexahydro-3-methyl-2,6-methano-9H-pyrrolo[3,2-h][3]benzazocine;

6,12-diethyl-1,2,3,4,5,6-hexahydro-3-methyl-2,6-methano-10H-pyrrolo[3,2-i][3]benzazocine;

6,12-diethyl-1,2,3,4,5,6-hexahydro-3-methyl-2,6-methano-9H-pyrrolo[2,3-j][3]benzazocine;

1,2,3,4,5,6-hexahydro-3-methyl-2,6-methano-9H-pyrrolo[3,2-h][3]benzazocine;

1,2,3,4,5,6-hexahydro-3-methyl-2,6-methano-10H-pyrrolo[3,2-i][3]benzazocine;

1,2,3,4,5,6-hexahydro-6,12-dimethyl-3-(2-phenylethyl)-2,6-methano-8H-pyrrolo[2,3-i][3]benzazocine;

1,2,3,4,5,6-hexahydro-6,12-dimethyl-3-(3-methyl-2-butenyl)-2,6-methano-9H-pyrrolo[3,2-h][3]benzazocine;

The 2,6-methanopyrrolo-3-benzazocines of this invention are useful as analgetics due to their ability to alleviate pain in mammals. The procedure employed to determine analgetic utility is a modification of the phenyl-p-quinone writhing assay in mice, a standard assay for analgesia [Proc. Soc. Exptl. Bio. Med., 95 729 (1957)]. In the modified procedure phenyl-p-benzoquinone (Eastman, 12.5 mg) is dissolved in 5 ml of 95% ethanol and the solution is diluted to a total volume of 100 ml with distilled water. The solution is administered to the subject mice subcutaneously at a dose of 10 ml per kg of body weight. A characteristic "writh", an inward rotation of one or more feet with twisting and turning of the trunk, drawing in of the abdominal wall, lordosis and arching of the back, is produced.

A total of 28 male mice (Charles River, CD-1), weighing 18 to 30 grams, are employed for a time response. The subject animals receive food and water ad libitum. Test compounds are dissolved in distilled water, or suspended in distilled water containing one drop of a suitable surfactant, such as Tween-80.

Four groups of five animals (20 animals) are given the test compound subcutaneously at 15, 30, 45 and 60 minutes prior to administration of the phenyl-p-quinone. Four control groups of 2 animals (8 animals) receive an equal volume of the vehicle. After the administration of the phenyl-p-quinone, the mice are place separately in one liter beakers, and after five minutes, are observed for ten minutes. The number of writhes for each animal is recorded. The following formula is used to compute the percent inhibition:

$$\frac{x \text{ Writhes in Control Group} - x \text{ Writhes in Drug Group}}{x \text{ Writhes in Control Group}} \times 100$$

The time period with the greatest percent of inhibition is considered the peak time. A dose range determination is generally reserved for those compounds which inhibit writhing by greater than 65-70% at the screening dose.

A dose range determination is run in the same manner as the time response except 10 animals per group are tested at the peak time of test drug activity. Fifty animals, 4 test drug groups, and a vehicle control are employed. Animals are dosed and tested in a randomized manner. A calculated $ED_{50}$, i.e., the dose at which 50% inhibition of writhing is produced, is determined by a computer linear regression analysis. The calculated subcutaneous (s.c.) dose effecting an approximately 50% inhibition of writhing ($ED_{50}$) in mice produced in this assay is as follows:

| Compound | Analgesic Activity (Inhibition of Writhing $ED_{50}$ (mg/kg, s.c.) |
|---|---|
| 1,2,3,4,5,6-hexahydro-3,6,12-trimethyl-2,6-methano-8H-pyrrolo[2,3-i][3]benzazocine | 29.5 |
| 1,2,3,4,5,6-hexahydro-3,6,12-trimethyl-2,6-methano-9H-pyrrolo[2,3-j][3]benzazocine | 30.4 |
| 1,2,3,4,5,6,9,10-octahydro-3,6,12-trimethyl-2,6-methano-8H-pyrrolo[2,3-i][3]benzazocine. | 35.5 |
| 1,2,3,4,5,6-hexahydro-3,6,12-trimethyl-2,6-methanopyrrolo-[2,3-j][3]benzazocine-10,11(9H)-dione | 24.3 |
| 1,2,3,4,5,6-hexahydro-3,6,12-trimethyl-2,6-methano-9H-pyrrolo-[3,2-h][3]-benzazocine | 0.6 |
| 1,2,3,4,5,6-hexahydro-3,6,12-trimethyl-2,6-methano-10H-pyrrolo[3,2-i][3]-benzazocine | 1.8 |
| 10-chloro-1,2,3,4,5,6-hexahydro-3,6,12-trimethyl-2,6-methano-9H-pyrrolo[3,2-h][3]benzazocine | 0.08 |
| 1,2,3,4,5,6,7,8-octahydro-3,6,12-trimethyl-2,6-methano-9H-pyrrolo[3,2-h][3]benzazocine | 0.63 |
| 6,12-dimethyl-1,2,3,4,5,6-hexahydro-3-(2-phenethyl)-2,6-methano-9H-pyrrolo[3,2-h][3]benzazocine | 0.26 |
| 10-chloro-6,12-dimethyl-1,2,3,4,5,6-hexahydro-2,6-methano-9H-pyrrolo[3,2-h][3]benzazocine | 55% @ 20/mg/kg, sc |
| 10-chloro-6,12-dimethyl-1,2,3,4,5,6-hexahydro-3-(2-phenylethyl)-2,6-methano-9H-pyrrolo[3,2-h][3]benzazocine salicylate | 0.64 |
| 10-chloro-6,12-dimethyl-3-ethyl-1,2,3,4,5,6-hexahydro-2,6-methano-9H-pyrrolo[3,2-h][3]benzazocine | 0.94 |
| 10-chloro-6,12-dimethyl-1,2,3,4,5,6-hexahydro-3-(3-methyl-2-butenyl)-2,6-methano-9H-pyrrolo[3,2-h][3]benzazocine salicylate | 2.40 |
| 6,12-dimethyl-1,2,3,4,5,6,-hexahydro-2,6-methano-9H-pyrrolo[3,2-h][3]-benzazocine salicylate | 5.10 |
| 10-chloro-3-cyclopropylmethyl-6,12-dimethyl-1,2,3,4,5,6-hexahydro-2,6-methano-9H-pyrrolo-[3,2-h][3]benzazocine | 0.21 |
| 6,12-dimethyl-1,2,3,4,5,6-hexahydro-3-(3-methyl-2-butenyl)-2,6-methano-9H-pyrrolo[3,2-h][3]-benzazocine salicylate | 0.465 |
| 10-chloro-1,2,3,4,5,6-hexahydro-3,6,7,12-tetramethyl-2,6-methano-9H-pyrrolo[3,2-h][3]benzazocine | 1.05 |
| 3-cyclopropylmethyl-6,12-dimethyl-1,2,3,4,5,6-hexahydro-2,6-methano-9H-pyrrolo[3,2-h][3]benzazocine | 0.25 |
| 10-chloro-1,2,3,4,5,6-hexahydro-3-(2-phenylethyl)-6,7,12-trimethyl-2,6-methano-9H-pyrrolo[3,2-h][3]benzazocine salicylate | 0.70 |
| 3-(2-anilinoethyl)-6,12-dimethyl-1,2,3,4,5,6-hexahydro-2,6-methano-9H-pyrrolo[3,2-h][3]benzazocine salicylate | 22% @ 20 sc |
| 3-(2-anilinoethyl)-6,12-dimethyl-1,2,3,4,5,6,7,8-octahydro-2,6-methano-9H-pyrrolo[3,2-h][3]benzazocine salicylate | 30% @ 20 sc |
| 10-chloro-1,2,3,4,5,6,7,8-octahydro-3,6,12-trimethyl-2,6-methano-9H-pyrrolo[3,2-h][3]benzazocine | 1.00 |
| 6,12-dimethyl-1,2,3,4,5,6-hexahydro-3-(2-propenyl)-2,6-methano-9H-pyrrolo[3,2-h][3]benzazocine pentazocine | 81% @ 20 sc 1.3 |

Analgesia production is achieved when the 2,6-methano-pyrrolo-3-benzazocines of this invention are administered to a subject requiring such treatment as an effective oral, parenteral or intravenous dose of from 0.1 to 50 mg/kg of body weight per day. 2,6-Methanopyrrolo-3-benzazocines which achieve effective analgesia production at doses of about 5 mg/kg of body weight per day are particularly desirable. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Effective amounts of the present invention may be administered to a subject by any one of various methods, for example, orally as in capsules or tablets, parenterally in the form of sterile solutions or suspensions, and in some cases intravenously in the form of sterile solutions. 2,6-Methanopyrrolo-3-benzazocines of this invention, while effective themselves, may be formulated and administered in the form of their pharmaceutically acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

Effective quantities of the compounds of this invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0 and 300 milligrams of the active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, Promogel ™, cornstarch and the like; a lubricant such as magnesium stearate or Sterotex; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the preceeding type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and nontoxic in the amounts used.

For the purpose of parenteral therapeutic administration, the active compounds of this invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzylalcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

EXAMPLES

The following examples are for illustrative purposes only and are not to be construed as limiting the invention.

EXAMPLE 1

1,2,3,4,5,6-Hexahydro-3,6,12-trimethyl-2,6-methano-8H-pyrrolo[2,3-i][3]benzazocine

Step 1

A solution of 21.0 g of 3-ethoxycarbonyl-1,2,3,4,5,6-hexahydro-6,11-dimethyl-8-nitro-2,6-methano-3-benzazocine and 500 ml of methanol was hydrogenated over 5% palladium on barium sulfate (1.00 g) at 55 psig. Upon completion of the reaction, the solution was filtered free of solids and concentrated. The concentrate was dissolved in 300 ml of 5% aqueous hydrochloric acid and 370 ml of water, and treated with 59.3 g of anhydrous sodium sulfate and 14.5 g of hydroxylamine hydrochloride. After heating to reflux, the resulting solution was treated with a refluxing solution of 13.1 g of chloral hydrate and 89 ml of water. The reaction mixture was refluxed for an additional hour, cooled to 0° C., and basified to a pH of 8-9 by the addition of dilute aqueous ammonium hydroxide. The mixture was extracted with dichloromethane-ethyl acetate, washed with brine, dried over anhydrous magnesium sulfate and concentrated. The concentrate was dissolved in 432 ml of 10% aqueous sulfuric acid, warmed for 25-35 min in an oil bath (75°-78° C.), poured over ice, diluted with water, and extracted with dichloromethane. The extract was washed with brine, dried over anhydrous magnesium sulfate, filtered, and concentrated. The concentrate was purified by flash chromatography on silica gel, eluting with ethyl acetate/hexane to yield, as a major product, 3-ethoxycarbonyl-1,2,3,4,5,6-hexahydro-6,12-dimethyl-2,6-methanopyrrolo[2,3-i]-[3]benzazocine-9,10(8H)-dione and, as minor product, 3-ethoxycarbonyl-1,2,3,4,5,6-hexahydro-6,12-dimethyl-2,6-methanopyrrolo[3,2-h][3]benzazocine-7,8-(9H)-dione.

Step 2

To a stirred slurry of 2.92 g of lithium aluminum hydride in 85 ml of tetrahydrofuran, cooled to 0° C. under nitrogen, was added, via cannula, a solution of 1.00 g of 3-ethoxycarbonyl-1,2,3,4,5,6-hexahydro-6,12-dimethyl-2,6-methano pyrrolo[2,3-i][3]benzazocine-9,10(8H)-dione in 25 ml of tetrahydrofuran. The reaction mixture was refluxed for 3 hours, cooled to 0° C., and quenched with 28 ml of 10% aqueous tetrahydrofuran.

The aqueous mixture was then dried over anhydrous sodium sulfate, filtered, and concentrated. The concentrate was purified by means of flash chromatography (silica gel; utilizing as the eluent 2% triethylamine/0-4% methanol/ethylacetate) to yield 0.50 g (67%) of 1,2,3,4,5,6-hexahydro-3,6,12-trimethyl-2,6-methano-8H-pyrrolo[2,3-i][3]benzazocine.

Recrystallization from diethyl ether afforded the analytical sample, m.p. 150°-153° C.

Analysis: Calculated for $C_{17}H_{22}N_2$: 80.25% C., 8.74% H, 11.01% N. Found: 80.12% C., 8.89% N, 11.06% N.

EXAMPLE 2

1,2,3,4,5,6-Hexahydro-3,6,12-trimethyl-2,6-methanopyrrolo[2,3-j][3]benzazocine-10,11(9H)-dione.

To 46.28 g of a 2:1 molar mixture of 8-amino-1,2,3,4,5,6-hexahydro-3,6,11-trimethyl-2,6-methano-3-benzazocine and 9-amino-1,2,3,4,5,6-hexahydro-3,6,11-trimethyl-2,6-methano-3-benzazocine was added 770 ml of 5% aqueous hydrochloric acid, 950 ml of water, 151.16 g of anhydrous sodium sulfate, and 37.03 g of hydroxylamine hydrochloride. The resulting solution was heated to reflux at which time a solution of 33.29 g of chloral hydrate in 480 ml of water, also heated to reflux, was added. The reaction mixture was then refluxed for 1.2 hours, cooled to 0° C., basified to a pH of 8-9 by the addition of dilute ammonium hydroxide, and extracted with dichloromethane-ethyl acetate (having incorporated therein a small amount of methanol). The extract was washed with brine, dried over anhydrous magnesium sulfate, filtered free of inorganic salts, and concentrated. The concentrate was dissolved in 500 ml of 10% aqueous sulfuric acid and the resulting solution was then warmed for 25-30 minutes at a temperature of 70°-75° C. The solution was then poured over ice, basified by the addition of concentrated ammonium hydroxide, and extracted with dichloromethane. The extract was washed with brine, dried over anhydrous magnesium sulfate, filtered, and concentrated to afford a mixture of 1,2,3,4,5,6-hexahydro-3,6,12-trimethyl-2,6-methanopyrrolo[2,3-j][3]benzazocine-10,11(9H)-dione, 1,2,3,4,5,6-hexahydro-3,6,12-trimethyl-2,6-methano3-pyrrolo[3,2-i][3]benzazocine-8,9(10H)-dione, 1,2,3,4,5,6,-hexahydro-3,6,12-trimethyl-2,6-methanopyrrolo[3,2-h][3]benzazocine-7,8(9H)-dione, and 1,2,3,4,5,6-hexahydro-3,6,12-trimethyl-2,6-methanopyrrolo[2,3-i][3]benzazocine-9,10(8H)-dione. Flash chromatography of the isatin mixture (silica gel; eluting first with a solution of 1-2% triethylamine/0-5% methanol/ethylacetate, and then with 100% methanol) permitted partial separation of the components. The various fractions were then further purified by successive chromatographic separations under conditions as previously described. Trituration of the 1,2,3,4,5,6-hexahydro-3,6,12-trimethyl-2,6-methanopyrrolo[2,3-j][3]benzazocine-10,11(9H)-dione fraction with diethylether/pentane and recrystallization from dichloromethane yielded 2.30 g (5%) of product, m.p. 220°-222° C. (dec.)

Analysis: Calculated for $C_{17}H_{20}N_2O_2$: 71.79% C., 7.10% H, 9.85% N. Found: 71.47% C., 7.15% H, 9.80% N.

EXAMPLE 3

1,2,3,4,5,6-Hexahydro-3,6,12-trimethyl-2,6-methano-9H-pyrrolo[2,3-j][3]benzazocine To a stirred slurry of 11.35 g of lithium aluminum hydride and 700 ml of tetrahydrofuran, cooled to 0° C. under nitrogen, was added, via cannula, a solution of 8.50 g of 1,2,3,4,5,6-hexahydro-3,6,12-trimethyl-2,6-methanopyrrolo[2,3-j][3]benzazocine-10,11(9H)-dione. The reaction mixture was refluxed for 3 hours, cooled to 0° C., and quenched with 10% aqueous tetrahydrofuran. The aqueous mixture was then dried over anhydrous sodium sulfate, filtered, and concentrated. The concentrate was purified by means of flash chromatography (silica gel; 2% triethylamine/0-3% methanol/ethyl acetate) to yield 2.70 g (35%) of 1,2,3,4,5,6-hexahydro-3,6,12-trimethyl-2,6-methano-9H-pyrrolo[2,3-j][3]benzazocine.

Recrystallization from methanol-pentane afforded the analytical sample, m.p. 224°-227° C.

Analysis: Calculated for $C_{17}H_{22}N_2$: 80.25% C., 8.73% H, 11.01% N. Found: 79.92% C., 8.98% H, 11.03% N.

EXAMPLE 4

1,2,3,4,5,6,9,10-Octahydro-3,6,12-trimethyl-2,6-methano-9H-pyrrolo[2,3-j][3]benzazocine To a solution of 1.69 g of 1,2,3,4,5,6,-hexahydro-3,6,12-trimethyl-2,6-methano-9H-pyrrolo[2,3-j][3]benzazocine in 25 ml of acetic acid, cooled to 15° C. under nitrogen, was added 1.83 g of sodium cyanoborohydride. After stirring for 2 hours at 15°-20° C. the reaction mixture was quenched with 100 ml of water and basified to a pH of 12 by the addition of 50% aqueous sodium hydroxide.

The aqueous mixture was extracted with dichloromethane/diethyl ether and the combined organic extract was then washed with dilute aqueous sodium bicarbonate and brine, dried over anhydrous potassium carbonate, filtered and concentrated.

The concentrate was purified by flash chromatography (silica gel; 2% triethylamine/0-5% methanol/ethylacetate) to yield 1.50 g (88%) of 1,2,3,4,5,6,10,11-octahydro-3,6,12-trimethyl-2,6-methano-9H-pyrrolo[2,3-j][3]benzazocine.

The free base was dissolved in methanol, treated with ethereal hydrogen chloride and concentrated to precipitate the and corresponding dihydrochloride salt. The salt was redissolved in methanol and precipitated by the addition of diethylether to afford the hygroscopic product 1,2,3,4,5,6,10,11-octahydro-3,6,12-trimethyl-2,6-methano-9H-pyrrolo[2,3-j][3]benzazocine dihydrochloride 3:1 hydrate, mp 309°-311° C.

Analysis: Calculated for $C_{17}H_{26}N_2Cl_2.0.3H_2O$: 60.99% C., 8.03% H, 8.37% N. Found: 60.69% C., 8.07% H, 8.22% N.

EXAMPLE 5

1,2,3,4,5,6,9,10-Octahydro-3,6,12-trimethyl-2,6-methano-8H-pyrrolo[2,3-i][3]benzazocine To a stirred solution of 5.44 g of 1,2,3,4,5,6-hexahydro-3,6,12-trimethyl-2,6-methano-8H-pyrrolo-[2,3-i][3]benzazocine (see Example 1) in 56 ml of acetic acid, cooled to 15° C. under nitrogen, was added, 4.13 g of sodium cyanoborohydride. After stirring for 2.25 hours at 15°-18° C. the reaction mixture was quenched with 107 ml of water and basified to a pH of 12 by the addition of 50% aqueous sodium hydroxide.

The aqueous mixture was extracted with dichloromethane/diethyl ether and the combined organic extract was then washed with brine, dried over anhydrous sodium sulfate, filtered and concentrated. The concentrate was purified by flash chromatography (silica gel; 2% triethylamine/0-4.5% methanol/ethylacetate) to yield 4.38 g (80%) of 1,2,3,4,5,6,9,10-octahydro-3,6,12-trimethyl-2,6-methano-8H-pyrrolo[2,3-i][3]benzazocine.

Recrystallization from hexane afforded the analytical sample, m.p. 80°-83° C.

Analysis: Calculated for $C_{17}H_{24}N_2$: 79.62% C., 9.45% H, 10.93% N. Found: 79.44% C., 9.62% H, 11.01% N.

EXAMPLE 6

8-Acetyl-1,2,3,4,5,6,9,10-octahydro-3,6,12-trimethyl-2,6-methano-8H-pyrrolo[2,3-i][3]benzazocine To a solution of 6.33 g of 1,2,3,4,5,6,9,10-octahydro-3,6,12-trimethyl-2,6-methano-8H-pyrrolo[2,3-i][3]benzazocine, 70 ml of dichloromethane, 0.001 g of 4-dimethylaminopyridine and 6.90 ml of triethylamine, cooled to 0° C. under nitrogen, was added 2.63 ml of acetyl chloride. After stirring for 0.5 hour at room temperature, the reaction mixture was diluted by the addition of 170 ml of dichloromethane followed by dilute aqueous sodium hydroxide. Upon standing, the mixture separated into aqueous and organic layers. The organic layer was washed with dilute aqueous sodium bicarbonate. The combined aqueous layers were then back extracted with dichloromethane.

The combined organic layers were washed with brine, dried over anhydrous potassium carbonate, filtered and concentrated. Purification of the concentrate by means of column chromatography (florisil; dichloromethane) followed by washing through a pad of silica gel (5% triethylamine/10% methanol/dichloromethane) afforded a crude product which was triturated with 10–50% dichloromethane/pentane and recrystallized from dichloromethane to yield 2.50 g (34%) of 8-acetyl-1,2,3,4,5,6,9,10-octahydro-3,6,12-trimethyl-2,6-methano-8H-pyrrolo[2,3-i][3]benzazocine, m.p. 239.5°–242° C.

Analysis: Calculated for $C_{19}H_{26}N_2O$: 76.45% C., 8.80% H, 9.39% N. Found: 76.02% C., 8.80% H, 9.28% N.

EXAMPLE 7

8-Ethyl-1,2,3,4,5,6,9,10-octahydro-3,6,12-trimethyl-2,6-methano-8H-pyrrolo[2,3-i][3]benzazocine To a solution of 4.1 g of 8-acetyl-1,2,3,4,5,6,9,10,octahydro-3,6,12-trimethyl-2,6-methano-8H-pyrrolo[2,3-i][3]benzazocine in 100 ml of tetrahydrofuran, cooled to 0° C. under nitrogen, was added 1.04 g of lithium aluminum hydride. The reaction mixture was warmed to room temperature and then heated at reflux for 1.5 hours. After cooling to room temperature excess lithium aluminum hydride was destroyed by the addition of 10% aqueous tetrahydrofuran. The slurry was basified by the addition of dilute aqueous sodium hydroxide and filtered through a celite pad. Diethyl ether was then added. Upon standing, the mixture separated into aqueous and organic layers.

The aqueous layer was extracted with dichloromethane/diethyl ether. The combined organic layers were washed with brine, dried over anhydrous potassium carbonate, filtered, and concentrated.

The concentrate was twice purified by flash chromatography, (silica gel; 2% triethylamine/0–3% methanol/ethyl acetate) to afford 2.00 g (51%) of 8-ethyl-1,2,3,4,5,6,9,10-octahydro-3,6,12-trimethyl-2,6-methano-8H-pyrrolo[2,3-i][3]benzazocine.

Recrystallization from pentane yielded the analytical sample, m.p. 93.5°–96° C.

Analysis: Calculated for $C_{19}H_{28}N_2$: 80.21% C., 9.94% H, 9.85% N. Found: 80.32% C., 9.97% H, 9.59% N.

EXAMPLE 8

1,2,3,4,5,6-hexahydro-3,6,12-trimethyl-2,6-methano-10H-pyrrolo[3,2-i][3]benzazocine To a stirred slurry of 16.03 g lithium aluminum hydride in 1000 ml of tetrahydrofuran, cooled to 0° C. under nitrogen, was added, via cannula, a solution of 12.00 g of 1,2,3,4,5,6-hexahydro-3,6,12-trimethyl-2,6-methanopyrrolo[3,2-i][3]benzazocine8,9(10H)-dione (see Example 2) in 350 ml of tetrahydrofuran. After refluxing for 3 hours, the reaction mixture was cooled to 0° C. and quenched by the addition of 10% aqueous tetrahydrofuran. The mixture then dried over anhydrous sodium sulfate, filtered, and concentrated. The concentrate was purified by means of flash chromatography via a series of separations (silica gel, 2% triethylamine/0–5% methanol/ethyl acetate; alumina, 2% triethylamine/ethyl acetate; silica gel, 2% triethylamine/0–10%-methanol/ethyl acetate) to yield 3.00 g (28%) of 1,2,3,4,5,6-hexahydro-3,6,12-trimethyl-2,6-methano-10H-pyrrolo[3,2-i][3]benzazocine.

Recrystallization from dichloromethane-diethyl ether afforded the analytical sample, m.p. 225°–227° C.

Analysis: Calculated for $C_{17}H_{22}N_2$: 80.25% C, 8.74% H, 11.01% N. Found: 79.44% C, 9.55% H, 10.74% N.

EXAMPLE 9

1,2,3,4,5,6-hexahydro-3,6,12-trimethyl-2,6-methano-9H-pyrrolo[3,2-h][3]benzazocine.

To a stirred solution 0.42 of 3-ethoxycarbonyl-1,2,3,4,5,6-hexahydro-6,12-dimethyl-2,6-methanopyrrolo[3,2-h][3]benzazocine-7,8(9H)-dione (see Example 1) in 15 ml of tetrahydrofuran, cooled to 0° C. under nitrogen, was added 0.56 g of lithium aluminum hydride. After refluxing for 3 hours, the reaction mixture was cooled to 0° C. and quenched by the addition of 10% aqueous tetrahydrofuran. The mixture was then dried over anhydrous sodium sulfate, filtered and concentrated.

The above described reaction was repeated utilizing 0.67 g of the dione in 70 ml of tetrahydrofuran and adding 0.89 g of lithium aluminium hydride.

Purification of the combined concentrates by means of flash chromatography (silica gel, 2% triethylamine/0–2% methanol/ethyl acetate) afforded 0.36 g (44.5%) of 1,2,3,4,5,6-hexahydro-3,6,12-trimethyl-2,6-methano-9H-pyrrolo[3,2-h][3]benzazocine.

Trituration with dichloromethane-pentane afforded the analytical sample, m.p. 227°–229° C.

Analysis: Calculated for $C_{17}H_{22}N_2$: 80.25% C, 8.74% H, 11.01% N. Found: 79.72% C, 9.15% H, 11.23% N.

EXAMPLE 10

1,2,3,4,5,6,7,8-Octahydro-3,6,12-trimethyl-2,6-methano-9H-pyrrolo[3,2-h][3]benzazocine To a stirred solution of 2.24 g of 1,2,3,4,5,6-hexahydro-3,6,12-trimethyl-2,6-methano-9H-pyrrolo[3,2-h][3]benzazocine and 23 ml of acetic acid, cooled to 15° C. under nitrogen, was added 1.70 g of sodium cyanoborohydride. The reaction mixture was stirred for an additional 2 hr and 90 ml of water was added. The solution was made basic (pH 12) with 50% aqueous sodium hydroxide solution and extracted with dichloromethane-ether. The combined organic layers were washed with brine, dried over anhydrous potassium carbonate, filtered and concentrated. The residue was purified by flash chromatography (alumina, ether). Recrystallization from ether/pentane gave 1.55 g (69%) of product, mp 126°–128° C.

Analysis: Calculated for $C_{17}H_{24}N_2$: 79.62% C, 9.45% H, 10.93% N. Found: 79.38% C., 9.43% H, 10.84% N.

EXAMPLE 11

6,12-Dimethyl-1,2,3,4,5,6,7,8-octahydro-3-(2-phenethyl)-2,6-methano-9H-pyrrolo[3,2-h][3]benzazocine salicylate To a stirred solution of 2.95 g of 10-chloro-1,2,3,4,5,6-hexahydro-6,12-dimethyl-3-(2-phenethyl)-2,6-methano-9H-pyrrolo[3,2-h][3]benzazocine and 20.5 ml of acetic acid, cooled to 15° C. under nitrogen, was added 2.45 g of sodium cyanoborohydride. The reaction mixture was stirred for an additional 4.25 hr and water was then added. The solution was made basic (pH 12) with 50% aqueous sodium hydroxide solution. The mixture was extracted with ether and combined organic layers were washed with brine, dried over anhydrous potassium carbonate, filtered and concentrated. The residue was dissolved in 25 ml of acetic acid, flushed with nitrogen, 1.85 g of sodium cyanoborohydride was added, and the mixture was stirred for 18 hr at room temperature and worked up as above. The residue was purified by flash column chromatography (silica gel, 2% triethylamine/ether) to afford 1.82 g (61%) of 10-chloro-6,12-dimethyl-1,2,3,4,5,6,7,8-octahydro-3-(2-phenethyl)-2,6-methano-9H-pyrrolo[3,2-h][3]benzazocine, as a foam. The foam was dissolved in 30 ml of tetrahydrofuran, cooled to −78° C. under nitrogen, ammonia (about 150 ml) was condensed into the reaction flash, and an additional 35 ml of tetrahydrofuran was added. Sodium (0.41 g) was added and the resulting solution was stirred at −33° C. for 1 hr. The reaction mixture was quenched with solid ammonium chloride and the ammonia was allowed to evaporate. Water and dichloromethane were added and the layers were separated. The aqueous layer was extracted with dichloromethane and ether. The combined organic layers were washed with brine, dried over anhydrous potassium carbonate and filtered. The filtrate was concentrated. The residue was purified by flash chromatography (silica gel, 1% triethylamine/ether) to afford 1.10 g (70%) of product. The salicylate was prepared with 1.05 eg of salicyclic acid in ether. Addition of pentane precipitated the salt, mp 91°–94° C.

Analysis: Calculated for $C_{31}H_{36}N_2O_3$: 76.82% C, 7.50% H, 5.78% N. Found: 76.14% C, 7.28% H, 5.57% N.

EXAMPLE 12

3-(2-Anilinoethyl)-6,12-dimethyl-1,2,3,4,5,6,7,8-octahydro-2,6-methano-9H-pyrrolo[3,2-h][3]benzazocine salicylate To a stirred solution of 1.31 g of 3-(2-anilinoethyl)-6,12-dimethyl-1,2,3,4,5,6-hexahydro-2,6-methano-9H-pyrrolo[3,2-h][3]benzazocine and 10 ml of acetic acid, cooled to 15° C. under nitrogen, was added 0.70 g of sodium cyanoborohydride. The reaction mixture was stirred for an additional 2.5 hr at 15° C., and water was added. The solution was made basic (pH 12) with 50% aqueous sodium hydroxide solution. The mixture was extracted with ether and the combined organic layers were washed with brine, dried over anhydrous potassium carbonate and filtered. The filtrate was concentrated. The residue was purified by flash column chromatography (silica gel, 2% triethylamine/ether) to afford 1.24 g (94%) of product. The salicylate was prepared with 1.0 eg of salicyclic acid and had mp 183°–186° C.

Analysis: Calculated for $C_{31}H_{37}N_3O_3$: 74.52% C, 7.46% H, 8.41% N. Found: 74.82% C, 7.44% H, 8.42% N.

EXAMPLE 13

6,12-Dimethyl-1,2,3,4,5,6-hexahydro-3-(2-phenethyl)-2,6-methano-9H-pyrrolo[3,2-h][3]benzazocine To a stirred solution of 0.50 g of cyanogen bromide and 20 ml of chloroform was added, at room temperature with stirring, a solution of 1.0 g of 1,2,3,4,5,6-hexahydro-3,6,12-trimethyl-2,6-methano-9H-pyrrolo[3,2-h][3]benzazocine and 40 ml of chloroform. The mixture was heated at reflux for 2.6 hr, under nitrogen, and then cooled to room temperature. Dilute aqueous sodium bicarbonate solution was added and the layers were separated. The organic layer was washed with sodium bicarbonate solution. The combined aqueous layers were back extracted with ether, and the combined organic layers were washed with brine, dried over anhydrous potassium carbonate and filtered. The fitrate was concentrated. The residue was purified by flash chromatography (silica gel, 2% triethylamine/ether) to afford 0.73 g (70%) of 3-cyano-6,12-dimethyl-1,2,3,4,5,6-hexahydro-2,6-methano-9H-pyrrolo[3,2-h][3]benzazocine, which was combined with 0.39 g of the product from a previous reaction.

The nitrile (1.12 g) was dissolved in 60 ml of tetrahydrofuran and 0.80 g of lithium aluminium hydride was added, with cooling to 0° C. under nitrogen. The mixture was allowed to warm to room temperature and was then heated at reflux for 2 hr. The mixture was cooled to room temperature and 10% aqueous tetrahydrofuran was added. The mixture was filtered through anhydrous sodium sulfate and then celite. The filter cakes were washed with a mixture of triethylamine/methanol/ethyl acetate, and the filtrate was concentrated. The residue was purified by flash chromatography (alumina, triethyl amine/methanol/ether) to afford 0.70 g (69%) of 6,12-dimethyl-1,2,3,4,5,6-hexahydro-2,6-methano-9H-pyrrolo[3,2-h][3]benzazocine.

The amine (0.70 g) was dissolved in 15 ml of dimethylformamide and 0.80 g of potassium carbonate and 0.51 ml of diisopropylethylamine were added. 2-Phenethyl bromide (0.44 ml) was added dropwise at room temperature, under nitrogen, and the mixture was stirred at room temperature for 4 hr, followed by slow warming to 70° C. in an oil bath. The mixture was maintained at 70° C. for 10 min and then slowly cooled to room temperature. The reaction mixture was diluted with water, ethyl acetate was added, and the layers were separated. The aqueous layer was extracted with ethyl acetate, and the combined organic layers were washed with water, brine, dried over anhydrous potassium carbonate and filtered. The filtrate was concentrated. Trituration of the residue with pentane gave a 0.21 g (21%) of product, mp 173°–175° C.

Analysis: Calculated for $C_{24}H_{28}N_2$: 83.66% C, 8.21% H, 8.13% N. Found: 83.33% C, 8.42% H, 8.00% N.

EXAMPLE 14

6,12-Dimethyl-1,2,3,4,5,6-hexahydro-2,6-methano-9H-pyrrolo[3,2-h][3]-benzazocine salicylate To a stirred solution of 6.81 g of cyanogen bromide, 4.7 ml of diisopropylethylamine, and 142 ml of chloroform was added, at room temperature with stirring, a solution of 13.7 g of 1,2,3,4,5,6-hexahydro-3,6,12-trimethyl-2,6-methano-9H-pyrrolo[3,2-h][3]benzazocine and 414 ml of chloroform. The mixture was heated at reflux for 2.6 hr, cooled to room temperature, diluted with aqueous sodium bicarbonate solution, and the layers were separated. The organic layer was washed with sodium bicarbonate solution. The combined aqueous layers were extracted with ether. The combined organic layers were washed with brine, dried over anhydrous potassium carbonate, and filtered. Concentration of the filtrate followed by purification by flash chromatography (silica gel, 2% triethylamine/ethyl acetate) afforded 13.5 g (95%) of 3-cyano-6,12-dimethyl- 1,2,3,4,5,6-hexahydro-2,6-methano-9H-pyrrolo[3,2-h][3]benzazocine.

The nitrile (13.5 g) was dissolved in 790 ml of tetrahydrofuran and 9.65 g of lithium aluminum hydride was added with cooling to 0° C., under nitrogen. The mixture was allowed to warm to room temperature and was heated at reflux for 2 hr, under nitrogen. The mixture was cooled to room temperature and 9.7 ml of water dissolved in 87 ml tetrahydrofuran was added dropwise. After addition was complete, 9.7 ml of 15% aqueous sodium hydroxide solution and 29.1 ml of water were added. The mixture was filtered through anhydrous sodium sulfate and the celite. The filter cakes were washed with a mixture of triethyl amine/methanol/ethyl acetate and the residue was concentrated. The residue was purified by flash column chromatography (alumina, 0–50% methanol/ether to afford 4.00 g (52%) product. The salicylate was prepared with 1.05 eg of salicyclic acid in dichloromethane-ether. Recrystallization from methanol gave the salt, mp 275°–275.5° C.

Analysis: Calculated for $C_{23}H_{26}N_2O_3$: 72.99% C, 6.92% H, 7.40% N. Found: 72.97% C, 7.07% H, 7.48% N.

EXAMPLE 15

3-Cyclopropylmethyl-6,12-dimethyl-1,2,3,4,5,6-hexahydro-2,6-methano-9H-pyrrolo[3,2-h][3]benzazocine To a stirred solution of 3.22 g of 1,2,3,4,5,6-hexahydro-6,12-dimethyl-2,6-methano-9H-pyrrolo[3,2-h][3]benzazocine and 58 ml of dimethylformamide was added 4.70 ml of diisopropylethyl amine and then 1.56 ml of cyclopropylmethyl bromide, under nitrogen. The reaction mixture was warmed in an oil bath at 70°–80° C. for 1.5 hr and stirred at room temperature overnight. The reaction mixture was poured into water and ethyl acetate. The layers were separated and the aqueous layer was extracted with ethyl acetate and ether. The combined organic layers were washed with brine, dried over anhydrous potassium carbonate, filtered, and the filtrate was concentrated. The residue was purified by flash column chromatography (silica gel, 2% triethylamine/0–10% methanol/ethyl acetate) gave 2.48 g (63%) of product. Sublimation (173°–175° C., ~0.3 mm) gave the analytical sample, mp 187°–190° C. (dec).

Analysis: Calculated for $C_{20}H_{26}N_2$: 81.59% C, 8.90% H, 9.51% N. Found: 81.70% C, 8.87% H, 9.56% N.

EXAMPLE 16

6,12-Dimethyl-1,2,3,4,5,6-hexahydro-3-(2-propenyl)-2,6-methano-9H-pyrrolo[3,2-h][3]benzazocine To a stirred solution of 1.86 g of 6,12-dimethyl-1,2,3,4,5,6-hexahydro-2,6-methano-9H-pyrrolo[3,2-h][3]benzazocine and 40 ml of dimethylformamide was added 2.85 ml of diisopropylethyl amine. The mixture was cooled to 0° C. and 0.78 ml of allyl bromide in 5.0 ml of dimethylformamide was added, with stirring under nitrogen. The mixture was stirred at 0° for 4.5 hr and then poured into water and ethyl acetate. The layers were separated and the aqueous layer extracted with ethyl acetate and ether. The combined organic layers were washed with brine, dried over anhydrous potassium carbonate, filtered and, the filtrate was concentrated. The residue was purified by flash column chromatography on silica gel (2% triethylamine/0–10% methanol/ether) and on alumina (ether) to afford 1.02 g (47%) of product. Recrystallization from ether-pentane gave the analytical sample, mp 165°–168° C.

Analysis: Calculated for $C_{19}H_{24}N_2$: 81.38% C, 8.63% H, 9.99% N. Found: 81.55% C, 8.68% H, 9.89% N.

EXAMPLE 17

6,12-Dimethyl-1,2,3,4,5,6-hexahydro-3-(3-methyl-2-butenyl)-2,6-methano-9H-pyrrolo[3,2-h][3]benzazocine salicylate To a stirred solution of 0.78 g of 6,12-dimethyl-1,2,3,4,5,6-hexahydro-2,6-methano-9H-pyrrolo[3,2-h][3]benzazocine and 30 ml of dimethylformamide was added 1.13 ml of diisopropylethyl amine. The mixture was cooled to 0° C. and 0.58 g of 4-bromo-2-methyl-2-butene in 4.0 ml of dimethylformamide was added, with stirring under nitrogen. The mixture was stirred at 0° C. for an additional 2.5 hr and then poured into water and ethyl acetate. The aqueous layer was made basic (pH 8–10), with conc ammonium hydroxide solution. The layers were separated and the aqueous layer extracted with ethyl acetate and ether. The combined organic layers were washed with brine, dried over anhydrous potassium carbonate and filtered. The filtrate was concentrated. The residue was purified by flash column chromatography (silica gel, 2% triethylamine/ethyl acetate) to afford 0.38 g (38%) of product. The salicylate was prepared by dissolving the 0.59 g of product in 75 ml of ether, adding 0.278 g of salicyclic acid in 10 ml of ether, concentrating to 55 ml, and adding 10 ml of pentane, and had mp 168.5°–170° C.

Analysis: Calculated for $C_{28}H_{34}N_2O_3$: 75.31% C, 7.67% H, 6.27% N. Found: 75.61% C, 7.82% H, 6.46% N.

EXAMPLE 18

3-(2-Anilinoethyl)-6,12-dimethyl-1,2,3,4,5,6-hexahydro-2,6-methano-9H-pyrrolo[3,2-h][3]benzazocine salicylate To 2.78 g of 6,12-dimethyl-1,2,3,4,5,6-hexahydro-2,6-methano-9H-pyrrolo[3,2-h][3]benzazocine was added 50 ml of dimethylformamide and 4.05 ml of diisopropylethyl amine followed by 3.91 g of 2-anilinoethyl bromide hydrobromide at room temperature, with stirring under nitrogen. The reaction mixture was warmed slowly in an oil bath to 87° C. and the temperature was maintained at 87° C. for an additional 1 hr. The reaction mixture was diluted with water, ethyl acetate was added, and the layers were separated. The aqueous layer was extracted with ethyl acetate and ether. The combined organic layers were washed with brine, dried over anhydrous sodium sulfate and filtered. The filtrate was concentrated. The residue was purified by flash column chromatography (silica gel, 0.5% triethylamine/24.5% ether/hexane to 0.7% triethylamine/2% methanol, 31.3% ether/hexane) to afford 2.65 g (64%) of product. The salicyclate was prepared with 1.00 eg salicylic acid and had mp 209°–211° C.

Analysis: Calculated for $C_{31}H_{35}N_3O_3$: 74.82% C, 7.09% H, 8.44% N. Found: 74.72% C, 7.14% H, 8.41% N.

EXAMPLE 19

10-Chloro-1,2,3,4,5,6-hexahydro-3,6,12-trimethyl-2,6-methano-9H-pyrrolo[3,2-h][3]benzazocine To a stirred slurry of 5.24 g of lithium aluminum hydride and 337 ml of tetrahydrofuran, cooled to 0° C. under nitrogen, was added, a solution of 4.40 g of 10- chloro-1,2,3,4,5,6-hexahydro-3,6,12-trimethyl-2,6-methano[3,2-h][3]benzazocine7,8(9H)-dione (contaminated with about 40% of 8-amino-9-chloro-1,2,3,4,5,6-hexahydro-3,6,11-trimethyl-2,6-methano-3-benzazocine). The reaction mixture was warmed to room temperature and then heated at reflux for 2 hr. The reaction mixture was cooled, diluted with tetrahydrofuran, and quenched with 10% aqueous tetrahydrofuran. The mixture was filtered through anhydrous sodium sulfate and through celite. The filter cakes were washed with a mixture of 2% triethylamine/10% methanol/ethyl acetate, and the filtrate was concentrated. The residue was triturated with ether and the solid was purified by column chromatography (alumina, ether). Recrystallization from methanol-dichloromethane-pentane afforded 0.95 g (37%) of product, mp 221°-223° C.

Analysis: Calculated for $C_{17}H_{21}ClN_2$: 70.69% C, 7.34% H, 9.70% N. Found: 70.61% C, 7.33% H, 9.69% N.

EXAMPLE 20

10-Chloro-6,12-dimethyl-1,2,3,4,5,6-hexahydro-2,6-methano-9H-pyrrolo[3,2-h][3]benzazocine To a stirred solution of 1.68 g of cyanogen bromide and 35 ml of chloroform was added, at room temperature with stirring under nitrogen, a solution of 3.8 g of 10-chloro-1,2,3,4,5,6-hexahydro-3,6,12-trimethyl-2,6-methano-9H-pyrrolo[3,2-h][3]benzazocine and 100 ml of chloroform. The mixture was heated at reflux for 2 hr, under nitrogen, and cooled to room temperature. Dilute aqueous sodium bicarbonate solution was added and the layers separated. The organic layer was extracted with dilute aqueous sodium bicarbonate solution. The combined aqueous layers were extracted with ether and the combined organic layers were washed with brine, dried over anhydrous potassium carbonate and filtered. The filtrate was concentrated and the residue was purified by flash column chromatography (silica gel, 2% triethylamine/ethyl acetate) to afford 6.41 g (78%) of 10-chloro-3-cyano-6,12-dimethyl-1,2,3,4,5,6-hexahydro-2-methano-9H-pyrrolo-[3,2-h][3]benzazocine.

The nitrile (6.41 g) was dissolved in 300 ml of tetrahydrofuran and, 4.06 g lithium aluminum hydride was added, with stirring. The suspension was heated at reflux for 2 hr and ethyl acetate, water, aqueous sodium hydroxide solution and water were added. The suspension was filtered and the filtrate was concentrated. The residue was triturated with ether and the solid was recrystallized from methanol to give 0.64 g (18%) of the product, mp 260°-263° C. (dec.).

Analysis: Calculated for $C_{16}H_{19}ClN_2$: 69.92% C, 6.98% H, 10.20% N. Found: 69.68% C, 7.04% H, 10.04% N.

EXAMPLE 21

10-Chloro-6,12-dimethyl-3-ethyl-1,2,3,4,5,6-hexahydro-2,6-methano-9H-pyrrolo[3,2-h][3]benzazocine 10-Chloro-3-cyano-6,12-dimethyl-1,2,3,4,5,6-hexahydro-2,6-methano-9H-pyrrolo[3,2-h][3]benzazocine (6.41 g) was dissolved in 300 ml of tetrahydrofuran, and with stirring, 4.06 g of lithium aluminum hydride was added, under nitrogen. The suspension was heated at reflux for 2 hr and ethyl acetate was added dropwise. To the mixture was added water, 15% aqueous sodium hydroxide solution, and water. The suspension was filtered, and the filtrate was concentrated. The residue was triturated with ether, the mother liquor was concentrated and 2-g portions of the residue were alkylated with phenethyl bromide and 4-bromo-2-methylbut-2-ene according to the procedures described in Examples 23 and 26 to give 0.35 g (20%) and 0.41 g (24%), respectively, of product. Column chromatography (alumina, ether) followed by recrystallization from dichloromethane-ether-pentane afforded the analytical sample, mp 208°-210° C. (dec.).

Analysis: Calculated for $C_{18}H_{23}ClN_2$: 71.37% C, 7.67% H, 9.25% N. Found: 71.30% C, 7.91% H, 9.08% N.

EXAMPLE 22

10-Chloro-1,2,3,4,5,6-hexahydro-3-(2-phenethyl)-6,7,12-trimethyl-2,6-methano-9H-pyrrolo[3,2-h][3]benzazocine salicylate To 0.98 g of 10-chloro-1,2,3,4,5,6-hexahydro-6,7,12-trimethyl-2,6-methano-9H-pyrrolo[3,2-h][3]benzazocine was added 20 ml of dimethylformamide and 1.19 ml of diisopropylethyl amine. 2-Phenylethyl bromide (0.61 ml) was added dropwise at room temperature, under nitrogen. The reaction mixture was warmed slowly to 85° C. and the temperature was maintained at 85°-88° C. for an additional 3.5 hr in an oil bath. The reaction mixture was diluted with water, ethyl acetate was added, and the layers were separated. The aqueous layer was extracted with ethyl acetate and ether. The combined organic layers were washed with brine, dried over anhydrous potassium carbonate and filtered. The filtrate was concentrated and the residue was purified by flash column chromatography (silica gel, ether) to afford 0.87 g (65%) of product. The salicylate was prepared with 1.1 eg of salicyclic acid and had mp 114°-117° C. (dec.).

Analysis: Calculated for $C_{32}H_{35}ClN_2O_3$: 72.37% C, 6.64% H, 5.27% N. Found: 72.34% C, 6.71% H, 5.17% N.

EXAMPLE 23

10-Chloro-6,12-dimethyl-1,2,3,4,5,6-hexahydro-3-(3-methyl-2-butenyl)-2,6-methano-9H-pyrrolo[3,2-h][2]benzazocine salicylate To a stirred solution 2.0 g of a mixture of about 1.15 g of 10-chloro-6,12-dimethyl-1,2,3,4,5,6-hexahydro-2,6-methano-9H-pyrrolo[3,2-h][3]benzazocine and about 0.85 g of 10-chloro-6,12-dimethyl-3-ethyl-1,2,3,4,5,6-hexahydro-2,6-methano-9H-pyrrolo[3,2-h][3]benzazocine in 35 ml of dimethylformamide was added 2.54 ml diisopropylethyl amine. The mixture was cooled to 0° C., the mixture 0.87 g of 4-bromo-2-methyl-2-butene in 5.0 ml of dimethylformamide was added, under nitrogen. The mixture was stirred for 1 hr and 20 min and was poured into dilute aqueous ammonium chloride solution and ethyl acetate. The layers were separated and the aqueous layer extracted with ethyl acetate and ether. The combined organic layers were washed with brine, dried over anhydrous potassium carbonate, filtered, and the filtrate was concentrated. The residue was purified by flash column chromatography (silica gel, 2% Et$_3$N/O-10% methanol/ethyl acetate) and a second column (alumina, ether) to afford 0.51 (35.5%) of product, as a foam.

The above described reaction, workup and purification procedures were repeated to afford 0.62 g of product. The salicylate was prepared by dissolving the product (1.04 g) from both reactions in ether, adding 0.399 g of salicyclic acid in 30 ml of ether, concentrating, and adding pentane. The salt was collected by filtration, washed with pentane and dried to afford 0.91 g (22.5%) of product, mp 102°–104° C.

Analysis: Calculated for: $C_{21}H_{27}ClN_2 \cdot C_7H_6O_3$: 69.90% C, 6.93% H, 5.82% N. Found: 69.61% C, 6.93% H, 5.74% N.

EXAMPLE 24

10-Chloro-3-cyclopropylmethyl-6,12-dimethyl-1,2,3,4,5,6-hexahydro-2,6-methano-9H-pyrrolo[3,2-h][3]benzazocine To a stirred solution of 2.2 g of 10-chloro-6,12-dimethyl-1,2,3,4,5,6-hexahydro-2,6-methano-9H-pyrrolo[3,2-h][3]benzazocine and 40 ml of dimethylformamide was added 3.2 ml of diisopropylethyl amine and 1.07 ml of cyclopropylmethyl bromide, under nitrogen. The reaction mixture was warmed in an oil bath maintained at 70°–77° C. Additional cyclopropylmethyl bromide (0.16 ml) was added, warming continued for a total of 3 hr, and the solution was poured into dilute aqueous ammonium chloride solution and ethyl acetate. The layers were separated and the aqueous layer extracted with ethyl acetate and ether. The combined organic layers were washed with brine, dried over anhydrous potassium carbonate and filtered. The filtrate was concentrated. The residue was purified by flash column chromatography (silica gel, 2% triethylamine/0–5% methanol/ethyl acetate) followed by recrystallization from ether/dichloromethane/pentane to afford 0.97 g (32%) of product. The product was combined with products from two other reactions. The combined material was recrystallized from dichloromethane and the sublimed (175°–180° C., about 0.2 mm) to give the analytical sample, mp 187°–190° C.

Analysis: Calculated for $C_{20}H_{25}ClN_2$: 73.04% C, 7.66% H, 8.52% N. Found: 72.96% C, 7.82% H, 8.63% N.

EXAMPLE 25

10-Chloro-1,2,3,4,5,6-hexahydro-3,6,7,12-tetramethyl-2,6-methano-9H-pyrrolo[3,2-h][3]benzazocine To 7.00 g of 10-chloro-1,2,3,4,5,6-hexahydro-3,6,12-trimethyl-2,6-methanopyrrolo[3,2-h][3]benzazocine-7,8-(9H)-dione and 280 ml of tetrahydrofuran, cooled to −78° C., was added dropwise, 52 ml (1.5M in toluene) of methylmagnesium bromide, under nitrogen. The mixture was stirred at −78° C. for an additional 1 hr, 50 mins and was allowed to warm slowly to 0° C., with stirring at 0° C. for an additional 35 min. Dilute hydrochloric acid was added, and the mixture was made basic (pH 8-10) with conc ammonium hydroxide solution. The mixture was extracted with dichloromethane and ether. The combined organic layers were washed with brine, dried over anhydrous magnesium sulfate and filtered. The filtrate was concentrated and the precipitate was collected. The mother liquor was concentrated and purified by flash column chromatography (silica gel, 2% triethylamine/0–10% methanol/ether) to afford a total of 5.2 g (71%) of 10-chloro-1,2,3,4,5,6-hexahydro-7-hydroxy-6,7,12-trimethyl-2,6-methanopyrrolo-9H-[3,2-h][3]benzazocin-8-one.

To 10-chloro-1,2,3,4,5,6-hexahydro-7-hydroxy-6,7,12-trimethyl-2, 6-methanopyrrolo-9H-[3,2-h][3]benzazocin-8-one was added 500 ml of tetrahydrofuran and then 5.0 g of lithium aluminum hydride at room temperature in two portions, under nitrogen. The mixture was heated at reflux for 3 hr 10 min and then cooled to 0° C. Aqueous tetrahydrofuran (10%) and anhydrous sodium sulfate was added to the suspension, and the solids were removed by filtration through celite. The filter cake was washed with a mixture of triethylamine-methanol-ethyl acetate and concentrated. The residue was purified by flash column chromatography (silica gel, 2% triethylamine/0–10% methanol/ether). The appropriate fractions were concentrated, and the precipitate was collected, washed with ether, and dried to afford 2.18 g (32.5%) of product, mp 262°–265° C. (dec.).

Analysis: Calculated for $C_{18}H_{23}ClN_2$: 71.39% C, 7.66% H, 9.25% N. Found: 71.18% C, 7.84% H, 9.10% N.

EXAMPLE 26

10-Chloro-6,12-dimethyl-1,2,3,4,5,6-hexahydro-3-(2-phenethyl)-2,6-methano-9H-pyrrolo[3,2-h][3]benzazocine salicylate To a stirred solution of 2.0 g of a mixture of about 1.15 g of 10-chloro-6,12-dimethyl-1,2,3,4,5,6-hexahydro-2,6-methano-9H-pyrrolo[3,2-h][3]benzazocine and about 0.85 g of 10-chloro-3-ethyl-1,2,3,4,5,6-hexahydro-6,12-dimethyl-2,6-methano-9H-pyrrolo[3,2-h][3]benzazocine in 35 ml of dimethylformamide was added 1.91 ml of diisopropylethyl amine and then 1.00 ml of 2-phenethyl bromide, dropwise at room temperature, under nitrogen. The reaction mixture was stirred an additional 3 hr, slowly warmed to 90° over 2 hr and then cooled to room temperature. The reaction mixture was poured into water and extracted with ethyl acetate. The combined organic layers were washed with dilute aqueous ammonium chloride solution, brine, dried over anhydrous potassium carbonate and filtered. The filtrate was concentrated and the residue was purified by flash column chromatography (silica gel, 2% triethylamine/0–5% methanol/ethyl acetate and a second column (alumina, ether) to afford an oil. The salicylate was prepared by dissolving the oil in about 25 ml of ether and adding 0.229 g of salicyclic acid in 25 ml ether. The mixture was concentrated to about 45 ml and pentane (50–60 ml) was added. The precipitate was collected, washed with pentane and dried to afford 0.66 g (31%) of product, mp 102°–104° C.

Analysis: Calculated for $C_{24}H_{27}ClN_2 \cdot C_7H_6O_3$: 72.00% C, 6.45% H, 5.42% N. Found: 71.79% C, 6.62% H, 5.33% N.

EXAMPLE 27

10-Chloro-1,2,3,4,5,6,7,8-octahydro-3,6,12-trimethyl-2,6-methano-9H-pyrrolo[3,2-h][3]benzazocine To a stirred solution of 1.50 g of 10-chloro-1,2,3,4,5,6-hexahydro-3,6,12-trimethyl-2,6-methano-9H-pyrrolo[3,2-h][3]benzazocine and 14 ml of acetic acid, cooled to 15° C. under nitrogen, was added, 1.00 g of sodium cyanoborohydride, with stirring. The reaction mixture was stirred an additional 6.75 hr and water was added. The solution was made basic (pH 12) with 50% aqueous sodium hydroxide solution. The mixture was extracted with ether and the combined organic layers were washed with brine, dried over anhydrous potassium carbonate and filtered. The filtrate was concentrated. The residue was dissolved in 15 ml acetic acid and, as above, treated with 1.63 g of sodium cyanoborohydride for 5 hr. The residue was purified by flash column chromatography (silica gel, 2% triethylamine/0–10% methanol/ether) to afford 1.04 g (69%) of product. Recrystallization from ether-dichloromethane afforded the analytical sample, mp 168°–170° C.

Analysis: Calculated for $C_{17}H_{23}ClN_2$: 70.21% C, 7.97% H, 9.63% N. Found: 69.98% C, 8.17% H, 9.48% N.

EXAMPLE 28

3-Cyclopropylmethyl-6,12-dimethyl-1,2,3,4,5,6-hexahydro-2,6-methano-9H-pyrrolo[2,3-j][3]benzazocine To a stirred solution of 2.05 g of 6,12-dimethyl-1,2,3,4,5,6-hexahydro-2,6-methano-9H-pyrrolo[2,3-j][3]benzazocine and 37 ml of dimethylformamide was added 2.23 ml of diisopropylethyl amine. Cyclopropylmethyl bromide (0.91 ml) was added, under nitrogen, and the reaction mixture was heated at 73°–75° C. for 3.75 hr. The mixture was cooled to room temperature and poured into ethyl acetate and water. The layers were separated and the aqueous layer was extracted with ethyl acetate and ether. The combined organic layers were washed with brine, dried over anhydrous potassium carbonate, filtered, and concentrated. The residue was purified by flash column chromatography (silica gel, 2% triethylamine/ethyl acetate) to afford 1.48 g (59%) of product. Recrystallization from ether gave the analytical sample, mp 151.5°–153.5° C.

Analysis: Calculated for $C_{20}H_{26}N_2$: 81.59% C, 8.90% H, 9.51% N. Found: 81.53% C, 8.82% H, 9.44% N.

EXAMPLE 29

3-Cyclopropylmethyl-6,12-dimethyl-1,2,3,4,5,6-hexahydro-2,6-methano-8H-pyrrolo[2,3-i][3]benzazocine To a stirred solution of 0.99 g of 6,12-dimethyl-1,2,3,4,5,6-hexahydro-2,6-methano-8H-pyrrolo[2,3-i][3]benzazocine and 18 ml of dimethylformamide was added 1.44 ml of diisopropylethyl amine. Cyclopropylmethyl bromide (0.48 ml) was added, under nitrogen, and the reaction mixture was heated at 82°–83° C. for 6 hr. The reaction mixture was cooled to room temperature and was poured into ethyl acetate and water. The layers were separated and the aqueous layer extracted with ethyl acetate and ether. The combined organic layers were washed with water and brine, dried over anhydrous potassium carbonate, filtered, and concentrated. The residue was purified by flash column chromatography (silica gel, 2% triethylamine/0–15% methanol/ethyl acetate), a second column (silica gel, 2% triethylamine/ethyl acetate), and a third column (silica gel, 1% triethylamine/ether) to afford 0.28 g (23%) of the product, as an oil, which crystallized upon trituration with ether. Recrystallization from ether-pentane gave the analytical sample, mp 164°–166° C.

Analysis: Calculated for $C_{20}H_{26}N_2$: 81.59% C, 8.92% H, 9.51% N. Found: 81.53% C, 9.04% H, 9.39% N.

EXAMPLE 30

6,12-Dimethyl-1,2,3,4,5,6-hexahydro-3-(3-methyl-2-butenyl)-2,6-methano-9H-pyrrolo[2,3-j][3]benzazocine salicylate To a stirred solution of 0.98 g of 6,12-dimethyl-1,2,3,4,5,6-hexahydro-2,6-methano-9H-pyrrolo[2,3-j][3]benzazocine and 30 ml of dimethylformamide was added 1.07 ml of diisopropylethyl amine. The mixture was cooled to 0° C., and 0.67 g of 4-bromo-2-methyl-2-butene and 5 ml of dimethylformamide was added, under nitrogen. The mixture was stirred at 0° C. for 1.25 hr and was poured into water and ethyl acetate. The layers were separated and the aqueous layer was extracted with ethyl acetate and ether. The combined organic layers were washed with brine, dried over anhydrous potassium carbonate, filtered, and concentrated. The residue was purified by flash column chromatography (silica gel, 1% triethylamine/49% ethyl acetate/hex) to afford 0.47 g (37%) of product, as a foam. The salicylate was prepared in methanol-ether with 1.0 eq of salicylic acid and had mp 184°–186° C.

Analysis: Calculated for $C_{28}H_{34}N_2O_3$: 75.31% C, 7.67% H, 6.27% N. Found: 75.25% C, 7.62% H, 6.28% N.

EXAMPLE 31

6,12-Dimethyl-1,2,3,4,5,6-hexahydro-3-(3-methyl-2-butenyl)-2,6-methano-8H-pyrrolo[2,3-i][3]benzazocine To a stirred solution of 1.42 g of 6,12-dimethyl-1,2,3,4,5,6-hexahydro-2,6-methano-8H-pyrrolo[2,3-i][3]benzazocine and 40 ml of dimethylformamide was added 1.54 ml of diisopropylethyl amine. The mixture was cooled to 0° C. and 0.97 g of 4-bromo-2-methyl-2-butene in 8 ml of dimethylformamide was added, under nitrogen. The mixture was stirred at 0° C. for an additional 1.25 hr, and was poured into water and ethyl acetate. The layers were separated and the aqueous layer was extracted with ethyl acetate and ether. The combined organic layers were washed with brine, dried over anhydrous potassium carbonate, filtered, and concentrated. The residue was purified by flash column chromatography (silica gel, 2% triethylamine/ethyl acetate) to afford 0.63 g (35%) of product, mp 62°–65° C.

Analysis: Calculated for $C_{21}H_{28}N_2$: 81.75% C, 9.17% H, 9.08% N. Found: 81.41% C, 9.07% H, 9.02% N.

EXAMPLE 32

6-12-Dimethyl-1,2,3,4,5,6-hexahydro-3-(2-phenethyl)-2,6-methano-8H-pyrrolo[2,3-i][3]benzazocine To a stirred solution of 1.01 g of 6,12-dimethyl-1,2,3,4,5,6-hexahydro-2,6-methano-8H-pyrrolo[2,3-i][3]benzazocine and 28 ml of dimethylformamide was added 1.10 ml of diisopropylethyl amine. 2-Phenethyl bromide (0.69 ml) was added, under nitrogen, and the reaction mixture was heated at 92°–94° C. for 1.25 hr. The mixture was cooled to room temperature and was poured into ethyl acetate and water. The layers were separated and the aqueous layer was extracted with ethyl acetate and ether. The combined organic layers were washed with brine, dried over anhydrous potassium carbonate, filtered and concentrated. The residue was purified by flash column chromatography (silica gel, 1% triethylamine/49% ethyl acetate/hexanes) and a second column (alumina, ether) to afford 0.35 g (24%) of product, mp 121°–123.5° C.

Analysis: Calculated for $C_{24}H_{28}N_2$: 83.66% C, 8.21% H, 8.13% N. Found: 83.29% C, 8.16% H, 7.98% N.

EXAMPLE 33

8-Chloro-1,2,3,4,5,6-hexahydro-3,6,12-trimethyl-2,6-methano-9H-pyrrolo[2,3-j][3]benzazocine To a mixture of 29.04 g of 9-amino-8-chloro-1,2,3,4,5,6-hexahydro-2,6-methano-3,6,11-trimethyl-3-benzazocine, 75 ml of 13% aqueous hydrochloric acid, 328 ml of water, 137 g of anhydrous sodium sulfate, and 19.9 g of chloral hydrate was added a solution of 24.2 g of hydroxylamine hydrochloride and 41 ml of water. The reaction mixture was heated at reflux for 2.5 hr, with stirring, and then cooled to room temperature. The solids were collected, washed with ether, and dried under vacuum. The mother liquor was made basic (pH 8-10) with conc ammonium hydroxide solution and extracted with dichloromethane and ether. The organic extracts were concentrated. The solid was added to 100 ml of conc sulfuric acid at 92°-94° C. over 5-10 min., with stirring, and the mixture was heated an additional 20 min. The extraction residue was dissolved in 20 ml of conc sulfuric acid and heated at 92°-94° C. for 20 min. The reaction mixtures were cooled, combined, and poured over ice. The mixture was made basic (pH 12) with 50% aqueous sodium hydroxide solution. The solids were dissolved by addition of methanol and ether. The layers were separated and the aqueous layer was extracted with ether. Concentration of the ether extracts gave unreacted 9-amino-8-chloro-1,2,3,4,5,6-hexahydro-3,6,11-trimethyl-2,6-methano-3-benzazoxcine. To the aqueous layer was added conc hydrochloric acid to pH 9, and the mixture was extracted with dichloromethane and ether. The combined organic layers were washed with brine, dried over anhydrous magnesium sulfate, filtered and concentrated to give 20.3 g (58%) of 8-chloro-1,2,3,4,5,6-hexahydro-3,6,12-trimethyl-2,6-methanopyrrolo[2,3-j][3]-benzazocine-10,11(9H)-dione.

To a solution of 20.3 g of the above benzazocindione and 1000 ml of tetrahydrofuran was added 12.1 g of lithium aluminum hydride. The mixture was heated at reflux, under nitrogen, for 3 hr., cooled, and excess lithium aluminum hydride was destroyed by slow addition of 121 ml of 10% aqueous tetrahydrofuran, 12 ml of 15% aqueous sodium hydroxide followed by 36 ml of water. The insolubles were removed by filtration through a pad of anhydrous sodium sulfate and the filter cake was washed with 2% triethylamine-ethyl acetate. The filtrate was concentrated. The residue was purified by flash column chromatography (silica gel, 2% triethylamine/O→5% methanol/ethyl acetate) to afford 6.4 g (20% overall yield) of product. Recrystallization from methanol/dichloromethane/ether/pentane gave the analytical sample, mp 263°-265° C.

Analysis: Calculated for $C_{17}H_{23}ClN_2$: 70.69% C, 7.34% H, 9.70% N. Found: 70.55% C, 7.25% H, 9.63% N.

EXAMPLE 34

10-Chloro-6,12-dimethyl-1,2,3,4,5,6-hexahydro-3-(2-propenyl)-2,6-methano-9H-pyrrolo[3,2-h][3]benzazocine To a stirred solution of 1.30 g of 10-chloro-6,12-dimethyl-1,2,3,4,5,6-hexahydro-2,6-methano-9H-pyrrolo[3,2-h][3]benzazocine, and 24 ml of dimethylformamide was added 1.69 ml of diisopropylethyl amine. Upon cooling to 0° C., the mixture was cooled to 0° C. and 0.45 ml of allyl bromide in 5.0 ml of dimethylformamide was added, under nitrogen. The mixture was stirred an additional 3 hr at 0° C. and was poured into water and ethyl acetate. The layers were separated and the aqueous layer was extracted with ethyl acetate and ether. The combined organic layers were washed with brine, dried over anhydrous potassium carbonate, filtered, and concentrated. The residue crystallized on standing. Recrystallization from ether with ether-pentane and pentane washing gave 0.75 g (47%) of product, mp 189°-191° C.

Analysis: Calculated for $C_{19}H_{23}ClN_2$: 72.47% C, 7.38% H, 8.90% N. Found: 72.38% C, 7.46% H, 8.87% N.

REACTION SCHEME A

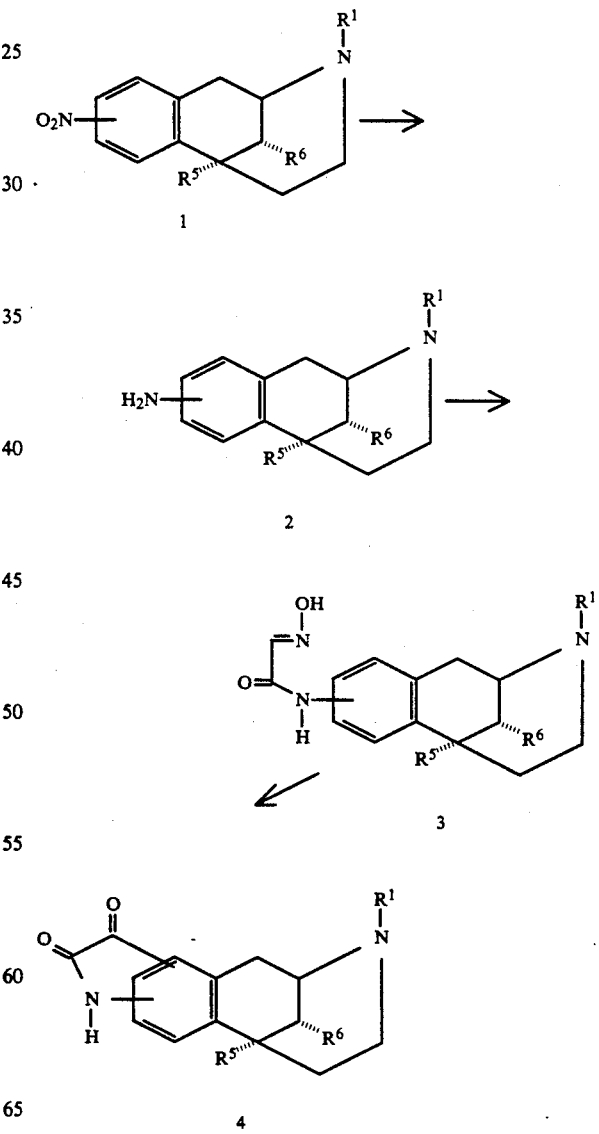

wherein $R^1$, $R^5$ and $R^6$ are as hereindefined.

REACTION SCHEME B
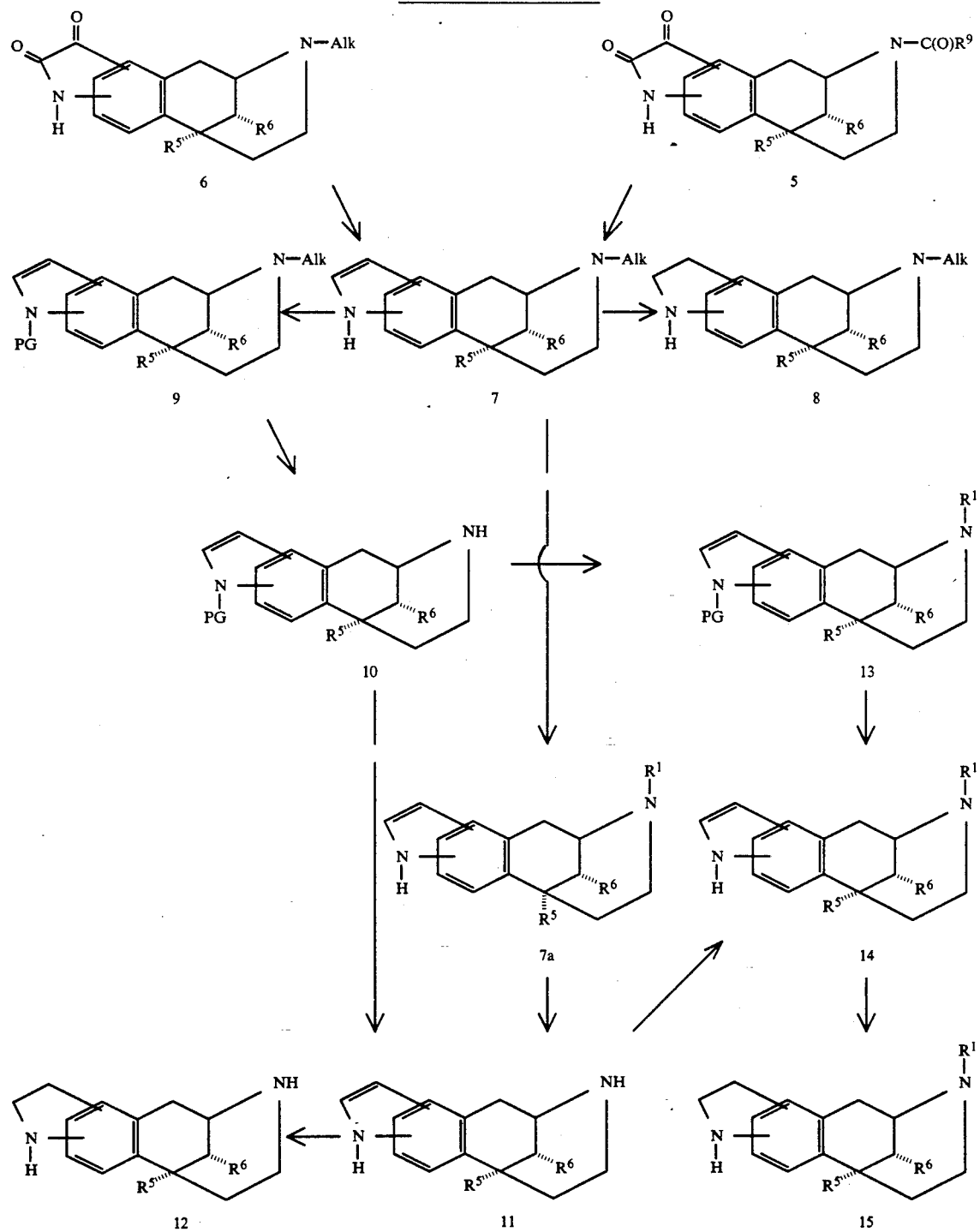
wherein Alk is loweralkyl or arylloweralkyl; $R^9$ is hydrogen, loweralkyl or loweralkoxy; $R^1$ is loweralkyl, loweralkenyl, cycloalkylloweralkyl or arylloweralkyl; $R^5$ and $R^6$ are independently hydrogen or loweralkyl or taken together are $-(CH_2)_4-$; and PG is a protecting group as hereindefined.
What is claimed is:
1. A compound of the formula
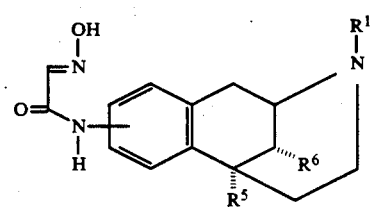

wherein $R^1$ is selected from the group consisting of hydrogen, loweralkyl, loweralkenyl, cycloalkylloweralkyl, arylloweralkyl, where the term aryl signifies a phenyl group optionally substituted by up to 3 substituents each of which is independently loweralkyl, loweralkoxy, halogen, trifluoromethyl, nitro or cyano, and —C(O)$R^9$ wherein $R^9$ is hydrogen, loweralkyl or loweralkoxy; and $R^5$ and $R^6$ are independently hydrogen or loweralkyl, or taken together are a bivalent radical of the formula —(CH$_2$)$_4$—.

* * * * *